(12) United States Patent
Ding et al.

(10) Patent No.: US 11,306,153 B2
(45) Date of Patent: Apr. 19, 2022

(54) ANTI-AXL TYROSINE KINASE RECEPTOR ANTIBODIES AND USES THEREOF

(71) Applicant: AGENCY FOR SCIENCE, TECHNOLOGY AND RESEARCH, Singapore (SG)

(72) Inventors: Mei Yee Vanessa Ding, Singapore (SG); Boon Hwa Andre Choo, Singapore (SG); Wey Jia Fong, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 343 days.

(21) Appl. No.: 16/303,657

(22) PCT Filed: May 22, 2017

(86) PCT No.: PCT/SG2017/050266
§ 371 (c)(1),
(2) Date: Nov. 20, 2018

(87) PCT Pub. No.: WO2017/200493
PCT Pub. Date: Nov. 23, 2017

(65) Prior Publication Data
US 2020/0317812 A1    Oct. 8, 2020

(30) Foreign Application Priority Data

May 20, 2016   (SG) ............................ 10201604090Y

(51) Int. Cl.
| | |
|---|---|
| *C07K 16/40* | (2006.01) |
| *A61K 47/68* | (2017.01) |
| *A61P 35/00* | (2006.01) |
| *A61K 39/00* | (2006.01) |
| *C07K 19/00* | (2006.01) |

(52) U.S. Cl.
CPC .......... *C07K 16/40* (2013.01); *A61K 47/6825* (2017.08); *A61P 35/00* (2018.01); *C07K 19/00* (2013.01); *A61K 39/00* (2013.01); *C07K 2317/24* (2013.01); *C07K 2317/31* (2013.01); *C07K 2317/565* (2013.01); *C07K 2317/622* (2013.01); *C07K 2317/626* (2013.01); *C07K 2319/00* (2013.01)

(58) Field of Classification Search
CPC ................................................ C07K 16/28–40
See application file for complete search history.

(56) References Cited

FOREIGN PATENT DOCUMENTS

| CN | 103998468 A | 8/2014 |
|---|---|---|
| WO | 2011159980 A1 | 12/2011 |
| WO | 2013064684 A1 | 5/2013 |
| WO | 2013064685 A1 | 5/2013 |
| WO | 2014174111 A1 | 10/2014 |
| WO | 2015095766 A2 | 6/2015 |
| WO | 2016005593 A1 | 1/2016 |
| WO | 2016187356 A1 | 11/2016 |
| WO | 2017189959 A1 | 11/2017 |

OTHER PUBLICATIONS

Edwards et al, J Mol Biol 334:103-118 (Year: 2003).*
Marchalonis et al., Dev & Comp Immunol 30:223-247 (Year: 2006).*
Almagro & Fransson, Frontiers in Bioscience 13:1619-33 (Year: 2008).*
Reichert & Valge-Archer, Nat. Rev. Drug Disc. 6:349-356 (Year: 2007).*
Tse et al., Clin Cancer Res 12(4):1373-82 (Year: 2006).*
The first Written Opinion for Singaporean Application No. 11201810355S dated Mar. 10, 2020, 9 pages.
Breij, et al., "Novel antibody-drug conjugates targeting Axl show anti-tumor activity in solid cancer xenograft models," American Association for Cancer Research Annual Meeting, Apr. 18-22, 2015, 1 page, American Association for Cancer Research.
The extended European Search Report for Application No. 17799791.3 dated Dec. 16, 2019, 6 pages.
Holliger, et al., "Engineered antibody fragments and the rise of single domains," Nature Biotechnology, Sep. 2005, 11 pgs., vol. 23, No. 9, Nature Publishing Group.
Ward, et al., "Binding activities of a repertoire of single immunoglobulin variable domains secreted from *Escherichia coli*," Nature, Oct. 12, 1989, pp. 544-546, vol. 341, Nature Publishing Group.
Liu et al., "Induction, regulation, and biologic function of Axl receptor tyrosine kinase in Kaposi sarcoma," Blood, 116(2): 297-305, 2010.
Liu et al., "Design, Synthesis, and Validation of Axl-Targeted Monoclonal Antibody," Mol. Pharm., 11(11): 3974-3979, 2014.
Kolbl et al., "The role of glycosylation in breast cancer metastasis and cancer control," Front. Oncol., 5(219): Jan. 5, 2015.
International Search Report and the Written Opinion of the International Searching Authority for International Application No. PCT/SG2017/050266 dated Aug. 8, 2018.
The Second Written Opinion for Singaporean Patent Application No. 11201810355S, dated Feb. 19, 2021, 8 pages.

(Continued)

*Primary Examiner* — Jessica H Roark
(74) *Attorney, Agent, or Firm* — Womble Bond Dickinson (US) LLP

(57) ABSTRACT

The present invention relates to antigen-binding proteins, or antigen-binding fragments thereof that bind to a glycan on the AXL receptor tyrosine kinase. The present invention also relates to antigen-binding proteins, or antigen-binding fragment conjugated to a radioisotope or cytotoxin, and wherein said antigen-binding proteins, or antigen-binding fragment is internalised into a cell upon binding to AXL receptor tyrosine kinase. Compositions comprising a physiologically acceptable carrier and a therapeutically effective amount of the antigen-binding protein, or antigen-binding fragment thereof, therapeutic use of the antigen-binding protein, or antigen-binding fragment thereof, methods for detecting cancer as well as kits when used in such methods are also provided.

18 Claims, 19 Drawing Sheets

Specification includes a Sequence Listing.

(56) References Cited

OTHER PUBLICATIONS

W. S. Sun; et al., "Coexpression of Growth Arrest-Specific Gene 6 and Receptor Tyrosine Kinases Axl and Sky in Human Uterine Endometrium and Ovarian Endometriosis"; Molecular Human Reproduction vol. 8, (2002); 7 pp.

Notification of the transmittal of the "International Preliminary Report on Patentability" of counterpart International Application No. PCT/SG2017/050266; dated Nov. 20, 2018; 9 pp.

The First Office Action for Chinese Application No. 201780044454.0 dated Aug. 12, 2021, 8 pages.

* cited by examiner

FIG. 1

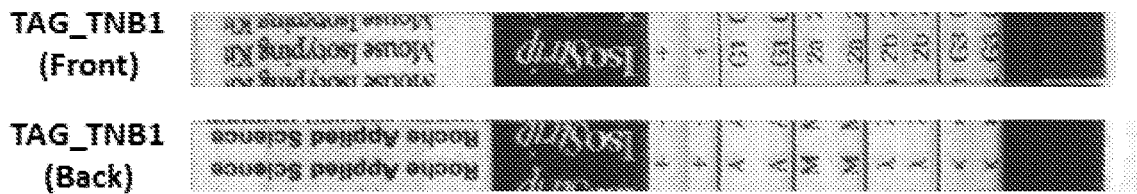

Gene Sequence (Heavy Chain) (SEQ ID NO: 12)
CAGGTCAAACTGCAGGAGTCAGGGGCTGAACTGGTGAAGCCTGGGGCTTCAGT
GAAGTTGTCCTGTAAGGCTTCTGGCTTCACCTTCACCAGCTACTATATGTACTGG
GTGAAGCAGAGGCCTGGACAAGGCCTTGAGTGGATTGGGGGGGTTAGTCCTAG
CAATGGTGGTGCTAACTTCAATGAGAAGTTCAAGACCAAGGCCACACTGACTGT
AGACAAATCCTCCAGCACAGCCTACATGCAACTCAGCAGCCTGACATCTGAGGA
CTCTGCGGTCTATTACTGTACAAGATTCCTTTATGGTCCGAGGTACTTCGATGTC
TGGGGCCAAGGGACCACGGTCACCGTCTCCTCA

Gene Sequence (Light Chain) (SEQ ID NO: 13)
GACATTGAGCTCACCCAGTCTCCAGCTTCTTTGGCTGTGTCTCTAGGGCAGAGG
GCCACCATCTCCTGCAGAGCCAGCGAAAGTGTTGATAATTATGGCATTAGTTTTA
TGAACTGGTTCCAACAGAAACCAGGACAGCCACCCAAACTCCTCATTTATGGTG
CATCCAACCAGGGATCCGGGGTCCCTGCCAGGTTTAGTGGCAGTGGGTCTGGG
ACAGACTTCAGCCTCAACATCCATCCTATGGAGGAGGATGATACTGCAATGTAT
TTCTGTCAGCAAAGTAAGGAGGTTCCGTACACGTTCGGAGGGGGGACCAAGCT
GGAAATAAAAC

Protein Sequence (Heavy Chain) (SEQ ID NO: 1)
QVKLQESGAELVKPGASVKLSCKAS<u>GFTFTSYYMY</u>WVKQRPGQGLEWIG<u>GVSPSN
GGANFNEKFKT</u>KATLTVDKSSSTAYMQLSSLTSEDSAVYYCTR<u>FLYGPRYFDV</u>WG
QGTTVTVSS

Protein Sequence (Light Chain) (SEQ ID NO: 2)
DIELTQSPASLAVSLGQRATISC<u>RASESVDNYGISFMN</u>WFQQKPGQPPKLLIY<u>GASN
QGS</u>GVPARFSGSGSGTDFSLNIHPMEEDDTAMYFC<u>QQSKEVPYT</u>FGGGTKLEIK

AXL receptor tyrosine kinase peptide sequence- homo sapiens (Uniprot)

Long form    (SEQ ID NO: 14)

MAWRCPRMGRVPLAWCLALCGWACMAPRGTQAEESPFVGNPGNITGARGLTGTLR<u>CQLQV</u>
<u>QGEPPEVHWLR</u>DGQILELADSTQTQVPLGEDEQDDWIVVSQLRITSLQLSDTGQYQCLVF
LGHQTFVSQPGYVGLEGLPYFLEEPEDRTVAANTPFNLSCCQAQGPPEPVDLLWLQDAVPL
ATAPGHGPQRSLHVPGLNK<u>TSSFSCEAHNAK</u>GVTTSR<u>TATITVLPQQPR</u>NLHLVSRQPTE
LEVAWTPGLSGIYPLTHCTLQAVLSNDGMGIQAGEPDPPEEPLTSQASVPPHQLRLGSLH
PHTPYHIRVACTSSQGPSSWTHWLPVETPEGVPLGPPENISATRNGSQAFVHWQEPR<u>APL</u>
<u>QGTLLGYRLAYQGQDTPEVLMDIGLR</u>QEVTLELQGDGSVSNLTVCVAAYTAAGDGPWSLP
VPLEAWRP*GQAQPVHQL*VKEPSTPAFSWPWWYVLLGAVVAAACVLILALFLVHRRKKETR
YGEVFEPTVERGELVVRYRVRKSYSRR<u>TTEATLNSLGISEELK</u>EKLRDVMVDRHKVALGK
<u>TLGEGEFGAVMEGQLNQDDSILK</u>VAVKTMKIAICTR<u>SELEDFLSEAVCMKEFDHPNVMRL</u>
<u>IGVCFQGSERESFPAPVVILPFMK</u><u>HGDLHSFLLYSRLGDQPVYLPTQMLVKFMADIASGM</u>
<u>EYLSTK</u>RFIHRDLAARNCMLNENMSVCVADFGLSKK<u>IYNGDYYR</u>QGRIAKMPVK<u>WIAIES</u>
LADRVYTSK<u>SDVWSFGVTMWEIATRGQTPYPGVENSEIYDYLR</u>QGNRLK<u>QPADCLDGLYA</u>
<u>LMSRCWELNPQDRPSFTELREDLENTLK</u>ALPPAQEPDEILYVNMDEGGGYPEPPGAAGGA
DPPTQPDPK<u>DSCSCLTAAEVHPAGRYVLCPSTTPSPAQPADR</u>GSPAAPGQEDGA

Note:

1. *GQAQPVHQL* - difference between short and long isoforms of AXL

2. Results is a total of 10 Mass Spectrometry (MS) analysis (Both in-gel and in-solution digestion post IP); Underlined sequences are sequence that were identified by MS.

3. Approximately, 34.6% of the peptide were identified from the combined MS results.

AXL receptor tyrosine kinase peptide sequence- homo sapiens (Uniprot)

Long form  (SEQ ID NO: 15)

MAWRCPRMGRVPLAWCLALCGWACMAPRGTQAEESPFVGNPGNITGARGLTGTLR<u>CQLQV</u>
<u>QGEPPEVHWLR</u>DGQILELADSTQTQVPLGEDEQDDWIVVSQLRITSLQLSDTGQYQCLVF
LGHQTFVSQPGYVGLEGLPYFLEEPEDRTVAANTPFNLSCQAQGPPEPVDLLWLQDAVPL
ATAPGHGPQRSLHVPGLNK<u>TSSFSCEAHNAK</u>GVTTSR<u>TATITVLPQQPR</u>NLHLVSRQPTE
LEVAWTPGLSGIYPLTHCTLQAVLSNDGMGIQAGEPDPPEEPLTSQASVPPHQLR<u>LGSLH</u>
<u>PHTPYHIR</u>VACTSSQGPSSWTHWLPVETPEGVPLGPPENSATRNGSQAFVHWQEPR<u>APL</u>
<u>QGTLLGYRLAYQGQDTPEVLMDIGLR</u>QEVTLELQGDGSVSNLTVCVAAYTAAGDGPWSLP
VPLEAWRP*GQAQPVHQI*VKEPSTPAFSWPWWYVLLGAVVAAACVLILALFLVHRRKKETR
YGEVFEPTVERGELVVRYRVRKSYSRR<u>TTEATLNSLGISEELKEKLRDVMVDRHKVALGK</u>
<u>TLGEGEFGAVMEGQLNQDDSILKVAVKTMKIA</u>CTR<u>SELEDFLSEAVCMKEFDHPNVMRL</u>
<u>IGVCFQGSERESFPAPVVILPFMKHGDLHSFLLYSRLGDQPVYLPTQMLVKFMADIASGM</u>
<u>EYLSTKRFIHRDLAARNCMLNENMSVCVADFGLSKKIYNGDYYRQGRIAKMPVKWIAIES</u>
<u>LADRVYTSKSDVWSFGVTMWEIATRGQTPYPGVENSEIYDYLRQGNR</u><u>LKQPADCLDGLYA</u>
<u>LMSRCWELNPQDRPSFTELREDLENTLK</u>ALPPAQEPDEILYVNMDEGGGYPEPPGAAGGA
DPPTQPDPK<u>DSCSCLTAAEVHPAGRYVLCPSTTPSPAQPADR</u>GSPAAPGQEDGA

Note:

1. *GQAQPVHQI* - difference between short and long isoforms of AXL

2. Results is a total of 5 Mass Spectrometry (MS) analysis (Both in-gel and in-solution digestion post IP); Underlined sequences are sequence that were identified by MS.

3. Approximately, 41.8% of the peptide were identified from the combined MS results.

(D)

Fig. 6
(A)
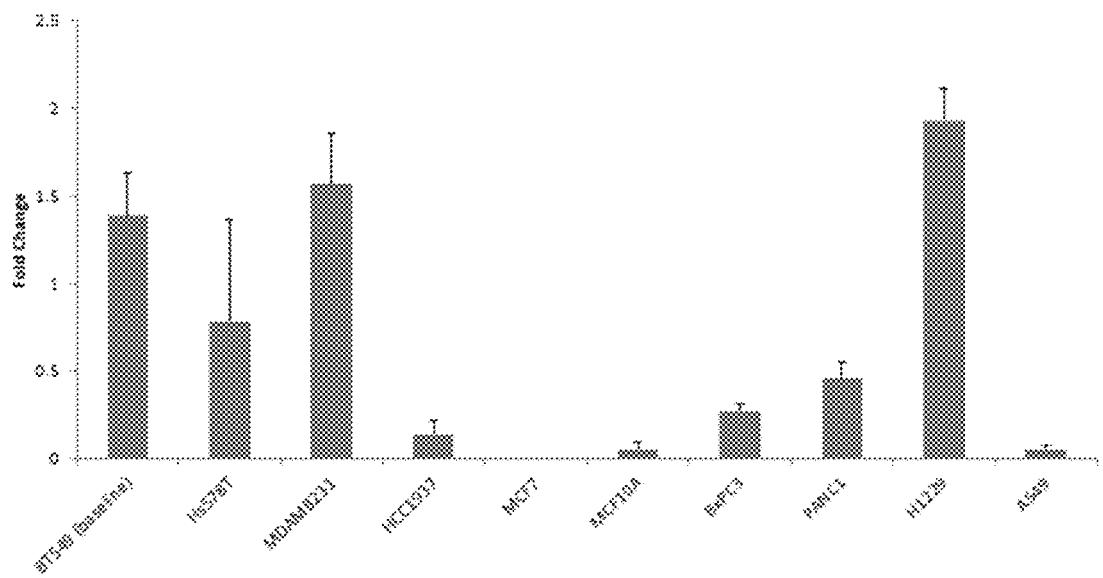
(B)
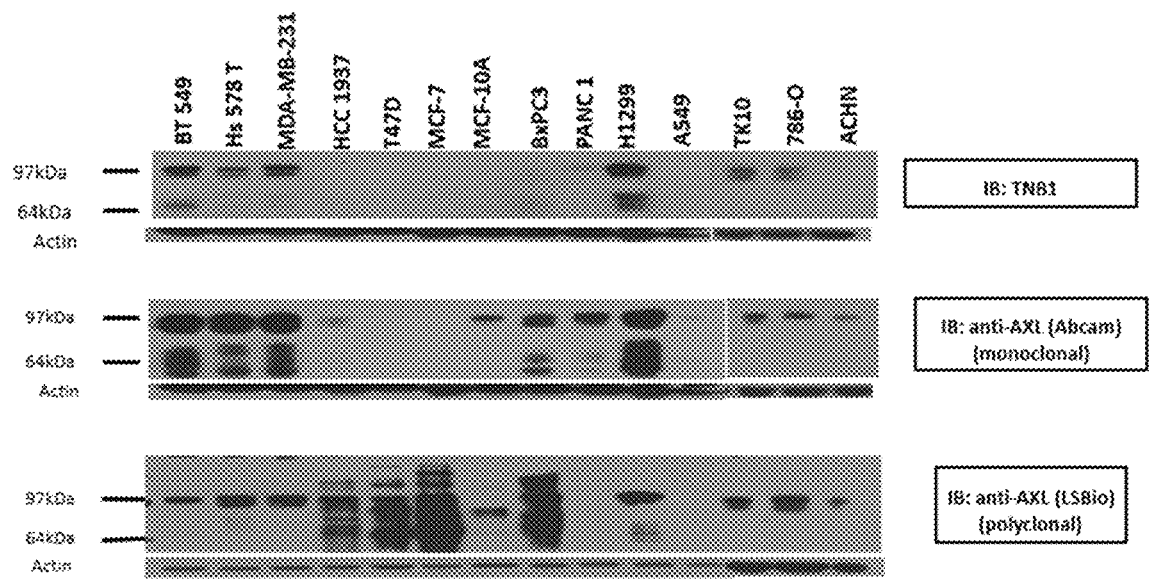

ANTI-AXL TYROSINE KINASE RECEPTOR ANTIBODIES AND USES THEREOF

CROSS-REFERENCE TO RELATED APPLICATIONS

This patent application is a U.S. National Phase Application Under 35 U.S.C. § 371 of International Application No. PCT/SG2017/050266, filed on 22 May 2017, entitled ANTI-AXL TYROSINE KINASE RECEPTOR ANTIBODIES AND USES THEREOF, which claims the benefit of priority of Singapore application no. 10201604090Y, filed 20 May 2016, the contents of which were incorporated by reference in the entirety for all purposes.

INCORPORATION BY REFERENCE

This patent application incorporates by reference the material (i.e., Sequence Listing) in the ASCII text file named 9322P145_Seq_List.txt, created on Nov. 20, 2018, having a file size of 24,576 bytes.

FIELD OF THE INVENTION

The present invention relates generally to antibodies. Specifically, the present invention relates to anti-AXL tyrosine kinase receptor antibodies and their uses thereof.

BACKGROUND OF THE INVENTION

Antibody-based therapy has in recent years become an important treatment strategy for cancer. Such therapy functions through mediating alterations in antigen or receptor function, modulating the immune system or delivering a specific drug that is conjugated to an antibody that targets a specific antigen.

The fundamental basis of antibody-based cancer therapy is the fact that cancerous tissues express an array of antigens that may be overexpressed, selectively expressed or mutated compared to normal, non-cancerous tissue. Antibodies against a specific antigen on a cancerous tissue can be used to target and kill the cancerous tissue.

However, a key challenge in developing candidate therapeutic antibodies for cancer is the identification of antigens suitable for antibody-based therapy. Suitability of an antigen for therapy is dependent on various factors including but not limited to the nature of the antigen (e.g. accessibility, abundance, location of expression on cancerous cells etc.), therapeutic approach, antibody affinity and other pharmacokinetic properties.

AXL receptor tyrosine kinase belongs to the TAM subfamily of receptor tyrosine kinases (RTKs) and overexpression has been detected in various cancers. Anti-AXL antibodies have been isolated and some anti-AXL antibodies are commercially available. However, none of these available anti-AXL antibodies bind to both surface and soluble AXL. Binding of these available anti-AXL antibodies are also not consistent across cancer cell lines. There is therefore a need to develop novel antibodies against AXL that address the disadvantages of the anti-AXL antibodies that are currently available.

SUMMARY

In one aspect, there is provided an antigen-binding protein, or an antigen-binding fragment thereof, comprising (i) a heavy chain variable domain comprising a VHCDR1 having the amino acid sequence GFTFTSYYMY (SEQ ID NO: 3); a VHCDR2 having the amino acid sequence GVSPSNGGANFNEKFKT (SEQ ID NO: 4), and a VHCDR3 having the amino acid sequence FLYGPRYFDV (SEQ ID NO: 5); and (ii) a light chain variable domain comprising a VLCDR1 having the amino acid sequence RASESVDNYGISFMN (SEQ ID NO: 6), a VLCDR2 having the amino acid sequence GASNQGS (SEQ ID NO: 7), and a VLCDR3 having the amino acid sequence QQSKEVP YT (SEQ ID NO: 8).

In one aspect, there is provided an antigen-binding protein, or an antigen-binding fragment thereof that competes with the antigen binding protein as defined herein for binding to AXL receptor tyrosine kinase.

In one aspect, there is provided an antigen-binding protein, or an antigen-binding fragment thereof, as defined herein, comprising a radioisotope or a cytotoxin conjugated thereto.

In one aspect, there is provided a composition comprising a physiologically acceptable carrier and a therapeutically effective amount of the antigen-binding protein, or antigen-binding fragment thereof as defined herein.

In one aspect, there is provided a use of an antigen-binding protein, or an antigen-binding fragment thereof as defined herein in the manufacture of a medicament for treating cancer.

In one aspect, there is provided a method for detecting cancer in a subject, the method comprising: contacting a sample obtained from the subject with an antigen-binding protein, or an antigen-binding fragment thereof as defined herein in vitro; detecting the binding of the antigen-binding protein, or antigen-binding fragment thereof in the sample; correlating the binding with a level of binding in a control sample to determine the level of binding in the sample, wherein an increase in the level of binding in the sample relative to the control sample is indicative of cancer.

In one aspect, there is provided a kit when used in the method as defined herein, comprising an antigen-binding protein, or an antigen-binding fragment thereof as defined herein, together with instructions for use.

Definitions

The terms "AXL receptor tyrosine kinase" and "AXL" are used interchangeably, and include variants, isoforms, species homologs of AXL receptor tyrosine kinase and analogs having at least one common epitope with AXL receptor tyrosine kinase.

The term "immune response" refers to the action of, for example, lymphocytes, antigen presenting cells, phagocytic cells, granulocytes, and soluble macromolecules produced by the above cells or the liver (including antibodies, cytokines, and complements) that results in selective damage to, destruction of, or elimination from the human body of invading pathogens, cells or tissues infected with pathogens, cancerous cells, or, in cases of autoimmunity or pathological inflammation, normal human cells or tissues.

The term "antigen binding protein" is used herein in the broadest sense to refer to molecules with an immunoglobulin-like domain which are capable of binding to an antigen and includes monoclonal, recombinant, polyclonal, chimeric, humanised, bispecific and heteroconjugate antibodies; a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

An "antibody" also refers to a glycoprotein comprising at least two heavy (H) chains and two light (L) chains interconnected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding fragment" of an antibody, as used herein, refers to one or more fragments of an antibody that retain the ability to specifically bind to an antigen (e.g., AXL tyrosine kinase receptor). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "high affinity" for an antibody refers to an antibody having a $K_D$ of $10^{-7}$ or less, $10^{-8}$ M or less, more preferably $10^{-9}$ M or less and even more preferably $10^{-10}$ M or less for a target antigen.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

BRIEF DESCRIPTION OF THE DRAWINGS

The invention will be better understood with reference to the detailed description when considered in conjunction with the non-limiting examples and the accompanying drawings, in which:

FIG. 1 shows isotyping of TAG_TNB1. Mouse monoclonal antibody of TAG_TNB1 was isotyped with an IgG2b heavy chain and a kappa light chain. Heavy and light chains of TNB1 were also sequenced for polypeptide and nucleotide sequences.

FIG. 6 shows the expression of AXL in TAG_TNB1 binding and non-binding cell lines. (A) mRNA expression of AXL. qRT-PCR shows consistently that the mRNA level for AXL is high in TAG-TNB1 binding cell lines (BT549, MDA-MB-231, Hs578T, and H1299) Primers used: 5'-GGTGGCTGTGAAGACGATGA-3' (Axl-5'; 1820-1839)[1] (SEQ ID NO: 9); 5'-CTCAGATACTCCATGC-CACT-3' (Axl-3'; 2103-2122)[1] (SEQ ID NO: 10)(B) Protein expression profile of AXL. Expression of AXL protein was markedly different with different commercial antibodies used (Abcam and LSBio). Protein binding profile of TAG_TNB1 was most similar to the results of mRNA compared to commercial antibodies. Binding of TAG_TNB1 also displayed less multi-band suggesting TAG-TNB1 is more specific. Actin was used a loading control.

DETAILED DESCRIPTION OF THE PRESENT INVENTION

Figure 2:
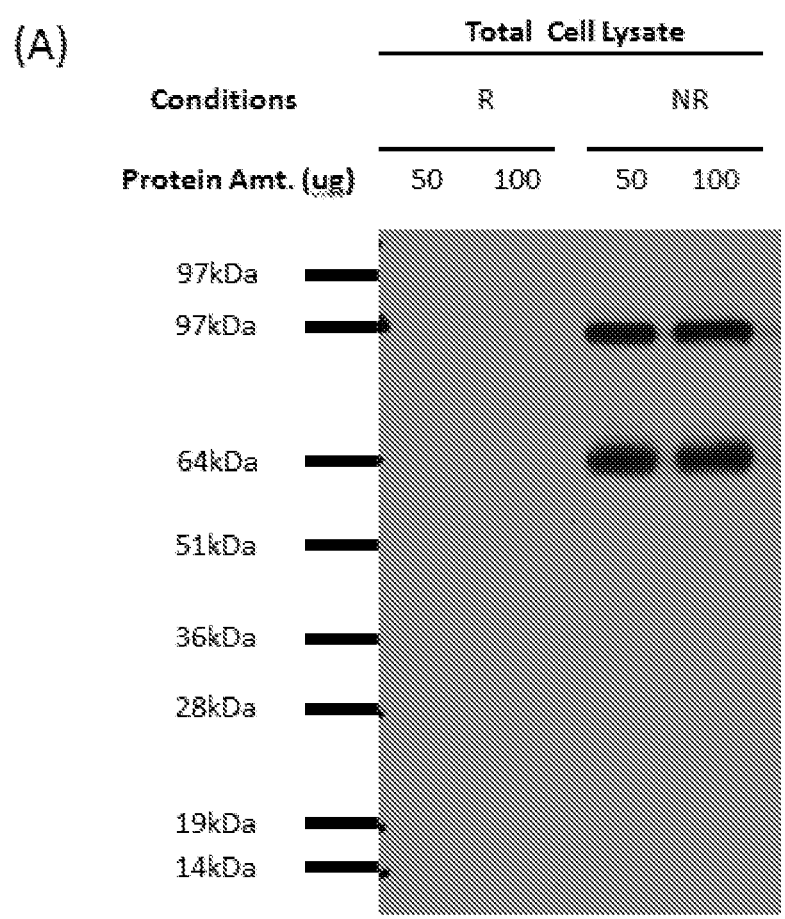
FIG. 2 shows determination of TAG_TNB1 antigen. (A) The antigen size was determined via Western blotting using total cell lysate of BT549 cell line. A doublet at ~97 kDa and 64 kDa was observed in the non-reduced condition. R=Reduced and NR=Non-reduced. (B) Immunoprecipitation (IP) of TAG_TNB1 bound antigen target with protein G-sepharose beads using BT549 cell lysate. Eluted IP product was run on SDS-PAGE gel and parallel sample was Western blotted. The IP product was excised from gel and processed for mass spectrometry analysis. (C) Mass spectrometry coverage for AXL with IP from TNBC (BT549) and NSCLC (H1299). Peptide coverage was approximately 35%-42% in the combined MS runs for BT549 and H1299 respectively. In note 1, the peptide corresponds to residues 429-437 of SEQ ID NO: 14 (for BT 549 cells) or SEQ ID No: 15 (for H1299 cells).
Figure 2:
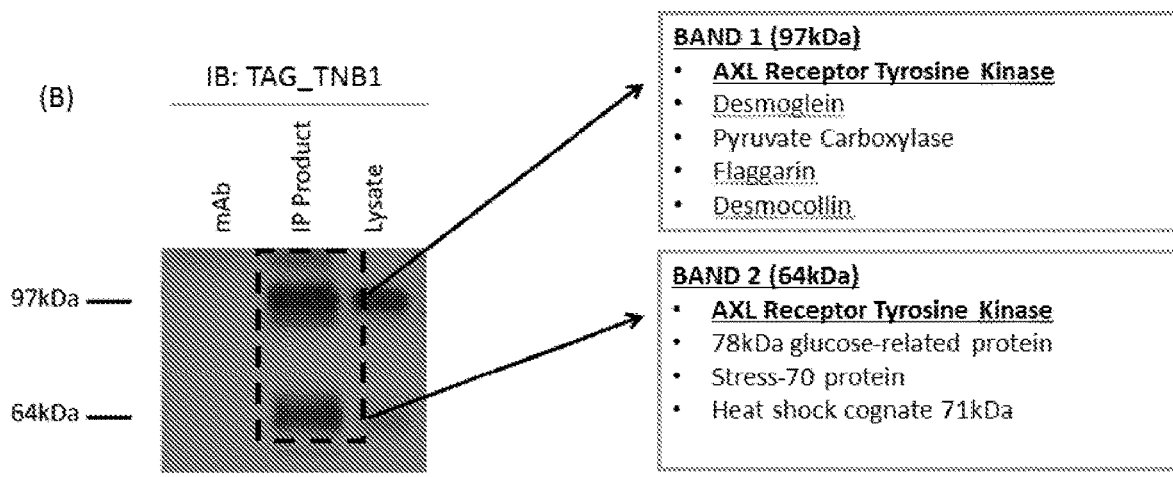

In a first aspect the present invention refers to an antigen-binding protein, or an antigen-binding fragment thereof, comprising (i) a heavy chain variable domain (VHCDR) comprising a VHCDR1 having the amino acid sequence GFTFTSYYMY (SEQ ID NO:3); a VHCDR2 having the amino acid sequence GVSPSNGGANFNEKFKT (SEQ ID NO: 4), and a VHCDR3 having the amino acid sequence FLYGPRYFDV (SEQ ID NO: 5); and (ii) a light chain variable domain (VLCDR) comprising a VLCDR1 having the amino acid sequence RASESVDNYGISFMN (SEQ ID NO: 6), a VLCDR2 having the amino acid sequence GASNQGS (SEQ ID NO: 7), and a VLCDR3 having the amino acid sequence QQSKEVP YT (SEQ ID NO: 8).

In one embodiment, the antigen-binding protein, or antigen-binding fragment thereof may comprise heavy and light chain CDR regions that are about 80%, about 85%, about 90%, about 95%, about 96%, about 97%, about 98% or about 99% identical to SEQ ID NO: 3, SEQ ID NO: 4, SEQ ID NO: 5, SEQ ID NO: 6, SEQ ID NO: 7 and SEQ ID NO: 8.

In a preferred embodiment, the heavy chain variable region of the antigen-binding protein, or an antigen-binding fragment thereof as disclosed herein may comprise the amino acid sequence set forth in SEQ ID NO:1.

In one embodiment, the antigen-binding protein, or antigen-binding fragment thereof as disclosed herein may comprise a heavy chain variable region which comprises an amino acid sequence having about 80%, about 85%, about 90%, about 95%, about 96%, about 97%, about 98% or about 99% identity to the amino acid sequence set forth in SEQ ID NO:1.

In another preferred embodiment, the light chain variable region of the antigen-binding protein, or antigen-binding fragment thereof as disclosed herein may comprise the amino acid sequence set forth in SEQ ID NO:2.

In another embodiment, the antigen-binding protein, or antigen-binding fragment thereof as disclosed herein may comprise a light chain variable region which comprises an amino acid sequence having about 80%, about 85%, about 90%, about 95%, about 96%, about 97%, about 98% or about 99% identity to the amino acid sequence set forth in SEQ ID NO:2.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences.

In one embodiment, the antigen-binding protein, or antigen-binding fragment thereof as disclosed herein may be selected from the group consisting of monoclonal, recombinant, polyclonal, chimeric, humanised, bispecific and heteroconjugate antibodies; a single variable domain, a domain antibody, antigen binding fragments, immunologically effective fragments, single chain Fv, a single chain antibody, a univalent antibody lacking a hinge region, a minibody, diabodies, and Tandabs™.

In a further embodiment, the binding protein may be a polyclonal or monoclonal antibody. In a preferred embodiment, the binding protein is a monoclonal antibody.

In a further preferred embodiment, the monoclonal antibody is TNB1. The monoclonal antibody may be humanized.

The antigen-binding protein, or antigen-binding fragment thereof of the present invention may bind to AXL receptor tyrosine kinase. In some embodiments, the antigen-binding protein, or antigen-binding fragment thereof may bind to a glycan on the AXL receptor tyrosine kinase. In a preferred embodiment, the glycan on the AXL receptor tyrosine kinase is located on the cell surface.

As used herein, glycan refers to a polysaccharide that may be homo- or hetero polymers of monosaccharides. Glycans include N-linked glycans and O-linked glycans. N-linked glycans are glycans whose monosaccharides are linked to the nitrogen in the side chain of asparagine. O-linked glycans are glycans whose monosaccharides are linked on a serine or threonine amino acid reside.

In a preferred embodiment, the antigen-binding protein, or antigen-binding fragment thereof binds to an O-linked glycan on the AXL receptor tyrosine kinase.

In another aspect, the present invention relates to an antigen-binding protein, or an antigen-binding fragment thereof, that competes with the antigen binding protein as disclosed herein for binding to AXL receptor tyrosine kinase. Competition with respect to binding may refer to binding affinity or to binding mechanism. For example, an antigen-binding protein, or an antigen-binding fragment thereof that competes with the antigen binding protein as disclosed herein for binding to AXL receptor tyrosine kinase may compete by binding to AXL with at least the same affinity or with higher affinity. Competitive binding may also be achieved by reducing avidity of binding. In another example, the antigen-binding protein, or antigen-binding fragment thereof that competes with the antigen binding protein as disclosed herein for binding to AXL receptor tyrosine kinase may compete by binding to glycans on AXL.

In another aspect, the present invention relates to an antigen-binding protein, or an antigen-binding fragment thereof as disclosed herein, conjugated to a therapeutic moiety, such as a cytotoxin, a drug (e.g., an immunosuppressant), a radioisotope or a radiotoxin.

Such conjugates are referred to herein as "immunoconjugates" or "antibody drug conjugates (ADCs)". Immunoconjugates that include one or more cytotoxins are referred to as "immunotoxins." A cytotoxin or cytotoxic agent includes any agent that is detrimental to (e.g., kills) cells. Examples include monomethyl auristatin E (MMEA-1), mertansine (DM-1) and saporin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to an antibody of the invention include duocarmycins, calicheamicins, maytansines and auristatins, and derivatives thereof.

In a preferred embodiment, the cytotoxin may be selected from the group consisting of monomethyl auristatin E (MMEA-1), mertansine (DM-1) and saporin.

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers.

Antibodies of the present invention also can be conjugated to a radioactive isotope (radioisotope) to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumour necrosis factor or interferon-gamma; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

In some embodiments, the antigen-binding protein, or antigen-binding fragment comprising a radioisotope or cytotoxin conjugated thereto may be internalized into a cell upon binding to AXL receptor tyrosine kinase. Internalization of the antigen-binding protein or antigen-binding fragment comprising a radioisotope or cytotoxin conjugated thereto releases the radioisotope or cytotoxin and may trigger cell death.

In some embodiments, the antigen-binding protein, or antigen-binding fragment thereof may trigger cell death by complement dependent cytotoxicity (CDC).

In another aspect, the present invention provides a composition comprising a physiologically acceptable carrier and a therapeutically effective amount of the antigen-binding protein, or an antigen-binding fragment thereof as disclosed herein.

Compositions may include one or a combination of (e.g., two or more different) antigen-binding protein, antigen-binding fragment thereof, antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. In some embodiments, the compositions of the present invention may comprise a further active pharmaceutical ingredient selected from the group consisting of bevacizumab, carboplatin, paclitaxel or gefitinib. In other embodiments, the compositions of the present invention may be administered with chemotherapy.

As used herein, "pharmaceutically acceptable carrier" or "physiologically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

The pharmaceutical compounds of the invention may include one or more pharmaceutically acceptable salts. A "pharmaceutically acceptable salt" or "physiologically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline metals or alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

In one aspect, there is provided the use of an antigen-binding protein, or an antigen-binding fragment thereof as disclosed herein in the manufacture of a medicament for treating cancer.

It will be generally understood that cancer treatment includes one or more of inhibiting growth of cancer cells, suppressing proliferation of cancer cells, trigging cell death, and activating host immune response to cancer cells.

Preferred cancers which may be treated using the antigen-binding protein, or antigen-binding fragment thereof as disclosed herein include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that may be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In a preferred embodiment, the cancer is selected from triple-negative breast cancer, non-small cell lung cancer, ovarian cancer, kidney cancer or pancreatic cancer.

In other embodiments, the medicament disclosed herein may be administered with a further active pharmaceutical ingredient. In some embodiments, the further active pharmaceutical ingredient is selected from the group consisting of bevacizumab, carboplatin, paclitaxel or gefitinib.

In yet other embodiments, the medicament disclosed herein may be administered with chemotherapy.

The further active pharmaceutical agent or chemotherapy may be administered separately, simultaneously or sequentially with the medicament, composition, antigen-binding protein, or antigen-binding fragment thereof as disclosed herein. Sequentially as used herein, refers to administration of the further active pharmaceutical agent or chemotherapy before or after administration of the medicament, composition, antigen-binding protein, or antigen-binding fragment thereof. Administration of the further active pharmaceutical agent or chemotherapy may take place immediately, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days or 7 days before and/or after administration of the medicament, composition, antigen-binding protein, or antigen-binding fragment thereof.

In another aspect, there is provided a method for detecting cancer in a subject, the method comprising: contacting a sample obtained from the subject with an antigen-binding protein, or an antigen-binding fragment thereof as disclosed herein in vitro; detecting the binding of the antigen-binding protein, or antigen-binding fragment thereof in the sample; correlating the binding with a level of binding in a control sample to determine the level of binding in the sample, wherein an increase in the level of binding in the sample relative to the control sample is indicative of cancer.

In some embodiments, the control sample is from the same subject. In some embodiments, the control sample is from a different subject.

In some embodiments, the antigen-binding protein, or antigen-binding fragment thereof to be used in the method for detecting cancer as disclosed herein, binds AXL receptor tyrosine kinase.

The antigen-binding protein, or antigen-binding fragment thereof to be used in the method for detecting cancer as disclosed herein may also comprise a detectable label.

As used herein, a detectable label includes fluorescent, chemiluminescent, phosphorescent and chromogenic labels. The label may be constitutively detectable, or may be detectable upon binding with a cell or substrate. Examples of detectable labels include but are not limited to Alexa Fluor® dyes, FITC, TRITC, PE, Texas Red, Cy® dyes, GFP, YFP, RFP, CFP, APC, R-PE, Qdot® probes, SYTOX Green, propidium iodide, biotin, horseradish peroxidase, alkaline phosphatase. In a preferred embodiment, the detectable label is selected from biotin, alkaline phosphatase, horseradish peroxidase, FITC, PE or Cy® Dyes.

The detectable label may be detected in an assay selected from flow cytometry, tissue section or immunohistochemistry.

In some embodiments, the cancer detected by the method as disclosed herein may be selected from melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer), refractory or recurrent malignancies whose growth may be inhibited using the antibodies of the invention, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In a preferred embodiment, the cancer detected by the method as disclosed herein may be selected from triple-negative breast cancer, non-small cell lung cancer, ovarian cancer, kidney cancer or pancreatic cancer.

In another aspect, there is provided a kit when used in the method as disclosed herein, comprising an antigen-binding protein, or an antigen-binding fragment thereof as disclosed herein, together with instructions for use.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

Experimental Section

Non-limiting examples of the invention and comparative examples will be further described in greater detail by reference to specific Examples, which should not be construed as in any way limiting the scope of the invention.

Materials and Methods

Isotyping

Isotyping was performed with Mouse Monoclonal Antibody Isotyping kit from Roche (Roche, #11493027001). The protocol was carried out according to manufacturer's instructions. Briefly, the pellet in the tube was reconstituted with 150 µl of hybridoma culture supernatant. The solution was thoroughly mixed by vortexing before adding the isostrip. The results were analyzed after 10 min of incubation.

Lysate Protein Extraction

Adherent BT549 and H1299 cells were scraped in ice cold PBS (Invitrogen, USA) and centrifuged at 1500 rpm for 5 minutes at 4° C. The pellet was suspended in Homogenize Buffer Mix made of 1:100 dilution of Protease Inhibitor Cocktail (Calbiochem-Novabiochem, UK) in 2% Triton and left on ice for 15 minutes. The cell lysate obtained was transferred to a 1.5 mL microcentrifuge tube and was centrifuged at 14,000 g for 1 minute at 4° C. The supernatant was collected and transferred to a new vial.

Protein Quantification Using DC Assay

Protein standards containing 0.2 mg/mL to 1.5 mg/mL of Bovine Serum Albumin were prepared. Samples were prepared by 10 times dilution of the sample lysate with 2% Triton/PBS. Standards and samples were added into microwells, at 5 µL per well. Reagent A' was made by adding reagent S (BioRad, USA) to reagent A (BioRad, USA) in a 1:50 dilution. Reagent A' was added into each well at 25 µL per well followed by 200 µL of reagent B (BioRad, USA). The plate was incubated in the dark at room temperature for 15 minutes. The protein in the samples was then quantified using Tecan I-control (Tecan, Switzerland) and a standard curve was generated.

Immunoprecipitation

Lysate protein extraction was carried out on BT549 and H1299 cells and the clarified cell lysate collected was used immediately for immunoprecipitation (IP). IP was carried out using the automated Phynexus MEA system (Phynexus, Inc., USA). Briefly, TAG_TNB1 was directly captured onto Protein G or Strepavidin PhyTip columns (5 µL resin bed). After washing away unbound proteins with Wash Buffer I (10 mM $NaH_2PO_4$/140 mM NaCl pH 7.4), clarified cell lysate was passed through the column functionalized with the mAb. The column was further washed with Wash Buffer II (140 mM NaCl pH 7.4), and bound proteins were eluted at low pH with Elution Buffer (200 mM $NaH_2PO_4$/140 mM NaCl pH 2.5) and neutralized immediately with 1 M Tris-Cl pH 9.0. The eluate was stored at 4° C. for further analysis.

Western Blot (i) Gel Electrophoresis

Protein loading dye was added to cell lysates or eluates from IP. The resultant mixture was boiled at 95° C. for 5 minutes. The electrophoresis apparatus was set up and the gel tank filled with MOPS buffer prepared with 5% MOPS SDS Running Buffer (NuPAGE) and 95% MilliQ water. SeeBlue Plus 2 molecular weight marker at 10 µL per well (Invitrogen, USA) and 26 µL of samples were loaded into the wells. The samples were separated by SDS-PAGE (NuPAGE 4-12% gradient gel, Invitrogen) followed by either Western blotting or silver staining.

(ii) Gel Transferring to Membrane

The transfer buffer was prepared with 20% methanol, 10% Tris-Glycine and 70% MilliQ water. The resolved proteins were transferred onto polyvinylidene fluoride (PVDF) membrane (Millipore, Mass.) and the transfer was carried out at 200V for 2 hours. The transferred membrane was stained with Ponceau-S stain (Sigma-Aldrich, Germany) for 30 seconds, and washed gently with MilliQ water to check for the appearance of bands and bubbles.

(iii) Immunoblotting

The blocking step was done by incubating the membrane in 5% milk for 30 minutes. After blocking, the membrane was incubated overnight with purified mAb diluted 1:200 with 2.5% milk. 1% BSA/PBS/0.1% Tween-20 (PBS-T) was used to wash the membrane 3 times for 5 minutes each before incubating in rabbit anti-mouse antibodies horseradish peroxidase-conjugated (1:10000, Dako). Lastly the membrane was washed 3 times in PBS-T, for 5 minutes each.

(iv) Chemiluminescent Detection

The membrane was transferred onto the Hypercassette (Amersham Biosciences, UK). Binding of HRP-conjugated secondary antibodies were visualized by ECL detection (GE Healthcare, Sweden).

Silver Staining and Liquid Chromatography-Mass Spectrometry

Silver staining was performed by fixing the gel in fixing solution (50% methanol and 5% acetic acid) for 30 minutes before hydrating with MilliQ water for 1 hour at room temperature. The gel was sensitized with 0.02% sodium thiosulphate for 2 minutes and washed 2 times with MilliQ water for 1 minute each. Cold silver nitrate was added and the gel incubated at 4° C. for 40 minutes. It was washed 2 times with MilliQ for 1 minute each before being developed in 0.04% formalin and 2% sodium carbonate with intensive shaking. After development, it was washed with 3.65 g/250 mL EDTA, $NO_2$ for 10 minutes and was rinsed 3 times in MilliQ water for 5 minutes each before being excised for liquid chromatography-mass spectrometry (LC-MS) analysis.

Antigen Target Validation

Validated siRNA targeted against AXL Receptor Tyrosine Kinase and non-targeting siRNA as negative control were purchased from Ambion (Ambion, Calif., USA) for use in experiments. Details of the siRNAs used are summarized in Table 1 below.

TABLE 1

Details of siRNA used

| Gene Target | Origin | siRNA ID | Target Sequence |
|---|---|---|---|
| AXL (Homo sapiens) | Ambion (Ambion, CA, USA) | s1847 | CAGCGAGAUUUAUGACUAUTT (sense) (SEQ ID NO: 11) |

$5 \times 10^5$ BT549 cells were seeded in each well of a 6-well plate 24 hours prior transfection. Wells with 60 to 80% cell confluency were transfected with siRNA using Lipofectamine reagent (Invitrogen, Carlsbad, USA) as transfection reagent according to manufacturer's protocol.

Mixtures with basal media (RPMI), lipofectamine and siRNA were prepared and incubated for 20 minutes at room temperature to allow siRNA complexes to be formed. Culture medium in each well was aspirated and replaced with fresh culture media (RPMI+10% FBS) before adding 200 μl of the siRNA complexes. The cells were incubated in 5% $CO_2$ atmosphere at 37° C. for 72 hours. After 72 hours, cells from each well were harvested, quantified, subjected to western blot procedures as described to analyze the silencing efficiency of the siRNA. The commercial AXL antibodies used to probe for the TAG-TNB1 antigen are shown in Table 2 below.

TABLE 2

Dilution of commercial primary and secondary antibody used for Western Blot

| Protein Target | Primary Antibody | Secondary Antibody |
|---|---|---|
| AXL Receptor Tyrosine Kinase | Mouse Monoclonal; ab54803 (1:1000; Abcam, Cambridge, UK) Polyclonal Rabbit AXL Antibody; Cat#: 10279 (1:1000; SINO Biological, BeiJing, China) Polyclonal Rabbit AXL Antibody; Cat#: PAB2998 (1:1000; ABNOVA, Taipei, Taiwan) Polyclonal Goat LSBIO. Cat#: LS-C149853 (1:1000; LSBIO, Seattle, USA) | Rabbit anti-Mouse IgG-HRP antibody; P0260 (1:10000, Dako) |

Flow Cytometry Analysis

Cells were harvested as single cell suspensions using trypsin, resuspended at $2 \times 10^5$ cells per 10 μL volume in 1% bovine serum albumin (BSA)/PBS and incubated for 30 minutes with each mAb clone (5 μL purified mAb). Cells were then washed with cold 1% BSA/PBS, and further incubated for 10 minutes in the dark with a 1:500 dilution of goat-mouse antibody fluorescein isothiocyanate (FTC)-conjugated (DAKO, Denmark). After incubation, the cells were again washed and resuspended in 200 μL of 1% BSA/PBS for analysis on a FACS Calibur (Becton, Dickinson and Company, USA).

Periodate Treatment

BT549 lysate and membrane protein fractions were subjected to gel electrophoresis and transfer to PVDF membrane as described above. After the membrane was blocked for 30 minutes in 5% milk, it was rinsed twice with 10 mL of 100 mM sodium acetate at pH 4.5. After that, the membrane was incubated with 5 mL of 100 mM sodium metaperiodate for 30 minutes in the dark at room temperature twice. Next, the membrane was rinsed four times with 10 mL of 100 mM sodium acetate, pH 4.5 and once with 10 mL PBS. The membrane was then incubated with 5 mL of 0.5M sodium borohydride for 30 minutes at room temperature. Following that the membrane was rinsed with 5 mL PBS, blocked with 5% milk again for 30 minutes and finally incubated with TNB1 mAb overnight. A control (non-treated) membrane was ran in parallel with the only difference being incubation with sodium acetate instead of sodium metaperiodate.

PNGase Digestion

PNGase digestion was carried out according to manufacturer's protocol (New England Biolabs). Briefly, 10-20 μg of glycoprotein was first denatured in 1× glycoprotein Denaturing Buffer at 95° C. for 10 minutes. Denatured proteins were then incubated with 1l sialidase at 37° C. Subsequently, 1×G7 Reaction Buffer and 10% NP-40 were added and incubated with increasing concentration of PNGase F at 37° C. for 1 hr. Digested proteins were subsequently resolved on SDS-PAGE and transferred to Western blot.

β-Elimination

Three membrane blots with different treatment would be carried out; (1) non treated [NT], (2) sodium hydroxide treated [SH] and (3) PBS treated as the negative control. NT blot was incubated overnight with 5% non-fat milk at 4° C. SH blot was incubated in 50 ml of 50 mM sodium hydroxide solution and PBS blot in 50 ml of 1×PBS at 42° C. overnight. On the next day, all blots were blocked with 5% non-fat milk, washed with 0.1% PBS/Tween for 3 times at 5 minutes intervals and then incubated with primary antibody overnight. Secondary antibody incubation and immunodetection was carried out on the third day using the Licor system.

Antibody-Dependent Cell-Mediated Cytotoxicity (ADCC) Assay

ADCC activity was measured using a reporter bioassay (Promega; ADCC Reporter Bioassay, # G7010). The ADCC bioassay was carried out according to the manufacturer's protocol Briefly, cells were seeded at 5,000 cells per well in a 96-well clear bottom black tissue culture plates (Corning; #3904) in low 4% IgG-serum (Promega; # G711A) media. Serial dilutions of primary antibody were incubated in triplicate wells for approximately 15 min at 37° C., 5% CO2. Following incubation, engineered effector cells were added to the wells at approximately 150,000 cells per well. After more than 5 h (or as indicated in results), Bio-Glo™ Luciferase Assay Substrate (Promega; # G719A and # G720A) was added to the wells and luminescence was measured using the Infinite® 200 microplate reader (Tecan).

Proliferation—Xcelligence Assay

Cells were seeded into an E-plate (Roche, Basel, Switzerland) (bottoms of each well have 80% of the surface area covered by interdigitated gold microelectrodes) at a density of 2500 cells per well and 90 uL per well. The plate was then incubated for 48 hours at 37° C. in humidified air with 5% $CO_2$. After 48 hours, 10 uL (1 mg/ml) of mAb or buffer was added to each well and the plate was again placed at 37° C. in humidified air with 5% $CO_2$. Cell growth was monitored using the xCELLigence System Real-Time Cell Analyzer (Roche, Basel, Switzerland) which measures the proliferation of adhered cells via cell conductance generated by impedance across the gold microelectrodes. Measurements were taken real time, from low cell numbers to confluency.

Proliferation—CellTiter-Glo Luminescent Cell Viability (CTG) Assay

Cells were seeded into a black coated 96 well plate (Grenier Bio-one, UK) at a range of density from 1000-5000 cells per well (depending on the cell type used) and 90 uL per well. The plate was then incubated for 24 hours at 37° C. in humidified air with 5% $CO_2$. After 24 hours, 10 uL of mAb or buffer was added to each well and the plate was again placed at 37° C. in humidified air with 5% $CO_2$. At t=0 hours, 3 days and 5 days after addition of mAb or buffer, 100 uL of CTG substrate (Promega, Wis., USA) was added to each well. The plate was then left in the dark for 10 minutes, with some shaking. The cell viability of the samples was then quantified using Tecan I-control (Tecan, Switzerland). CTG Assay provides a homogenous method for determining the number of viable cells (both adhered and in suspension) based on the quantitation of ATP, which indicates the presence of metabolically active cells.

Antibody Drug Conjugates (ADCs)

Chimeric TAG_TNB1 mAb were directly conjugated with Saporin toxin (Advanced Targeting Systems, San Diego, USA). Briefly, cells were seeded on the 96 well as described above in the CTG assay and ADC conjugated ch_TAG_TNB1-saporin was dosed into each well at a concentration range of 0-4.5 ug/ml. The cell viability of the cells was measure 5 days post treatment as described previously.

In Vivo Model

The antibody drug conjugate was prepared (Advanced Targeting Systems) as described earlier. For the animal model, the pre-emptive model was adopted. Each nude mouse was injected in the right flank, subcutaneously, with $5 \times 10^6$ H1299 cells in 100 μL volume PBS/matrigel (1:1 volume; BD Matrigel™ Matrix, #354234). The drug (40 μg per dose) was administered intra-peritoneal at Day 0, 7 and 14. Tumour size was monitored over 40 days. An IgG isotype ADC drug conjugate was used as control.

Results and Discussion

TAG_TNB1 is an IgG2b monoclonal antibody (mAb) raised against Triple Negative Breast Cancer (TNBC) cell line, BT549. The mAb was found to bind preferentially to cell surface of multiple TNBC cell lines as determined by flow cytometry. TAG_TNB1 was raised by immunizing the animal with intact cells hence characterization of the antigen target for TAG_TNB1 is needed. Characterization of TAG_TNB1 is beneficial to discern its therapeutic or diagnostic value in treating TNBC patients.

TAG_TNB1 bound to two distinct bands at ~97 kDa and 64 kDa demonstrated using total lysate of BT549 cells via Western blotting in FIG. 2(A). In addition, binding of the antibody was only observed in the non-reducing condition suggesting that the antibody recognises a conformational epitope. Immunoprecipitation (IP) was performed to enrich for the antigen target to facilitate target antigen identification using mass spectrometry (MS). As shown in FIG. 2B, and antigen target was enriched from IP, and the corresponding band in a parallel gel was excised, samples were digested with trypsin and analysed using MS. Results from MS suggest that the antigen target of TAG_TNB1 was most likely to be AXL tyrosine kinase receptor. Multiple IP-MS runs of the samples were performed using two cells lines, BT549 (TNBC) and H1299, a Non-Small Cells Lung Cancer (NSCLC) cell line. The sequence coverage was analysed and found that at least 35% and 42% of peptide sequence of AXL receptor tyrosine kinase had been identified from the combined MS results for BT549 and H1299 respectively.

Figure 3:
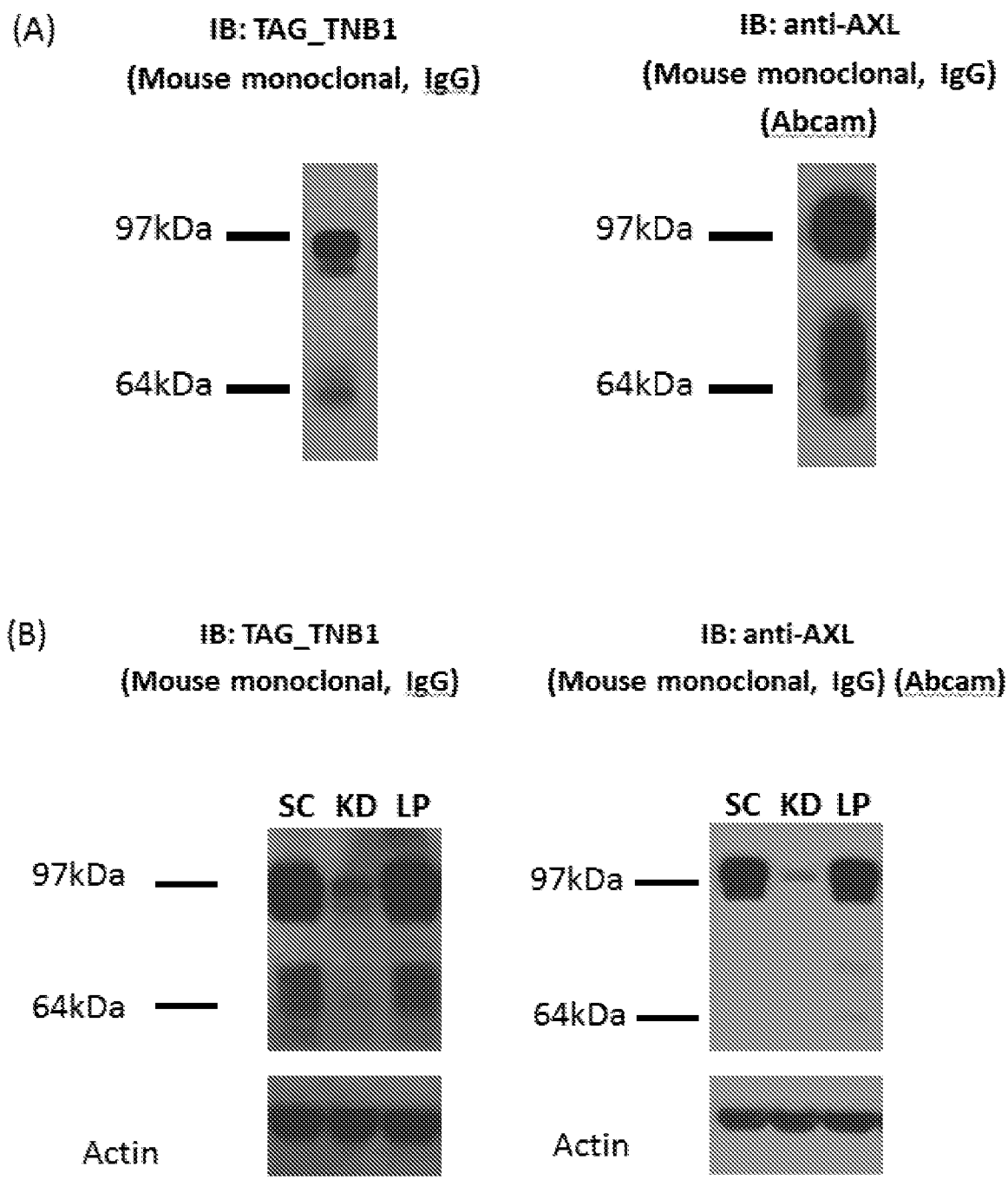
FIG. 3 shows that TAG_TNB1 binds to AXL protein. (A) Immunoblotting with both TAG_TNB1 and anti-AXL commercial antibody observed similar doublet band (ABCAM. Cat #: ab54803) using BT549 cell lysate. (B) Transient knockdown of AXL via siRNA. Both TAG_TNB1 and anti-AXL showed significant reduction of signal intensity compared to the controls (SC and LP). SC: Scrambled sequence, KD: Knockdown with AXL targeting sequence; LP: Lipofectamine reagent control. Actin was used as loading control.

The antigen target was validated using commercial anti-AXL antibody. Immunoblotting of commercial anti-AXL antibody also show similar bands at ~97 kDa and 64 kDa suggesting that TAG_TNB1 is binding to AXL receptor tyrosine kinase (FIG. 3A). Results from transient knockdown of AXL using siRNA confirmed that AXL is the target antigen of TAG_TNB1 where a significant reduction in the antigen band was observed compared to knockdown using the scrambled sequence control and the lipofectamine reagents (FIG. 3B). The transient knockdown of AXL protein was determined using the commercial anti-AXL antibody. Actin was used as loading control showing even loading between all samples.

Figure 4:
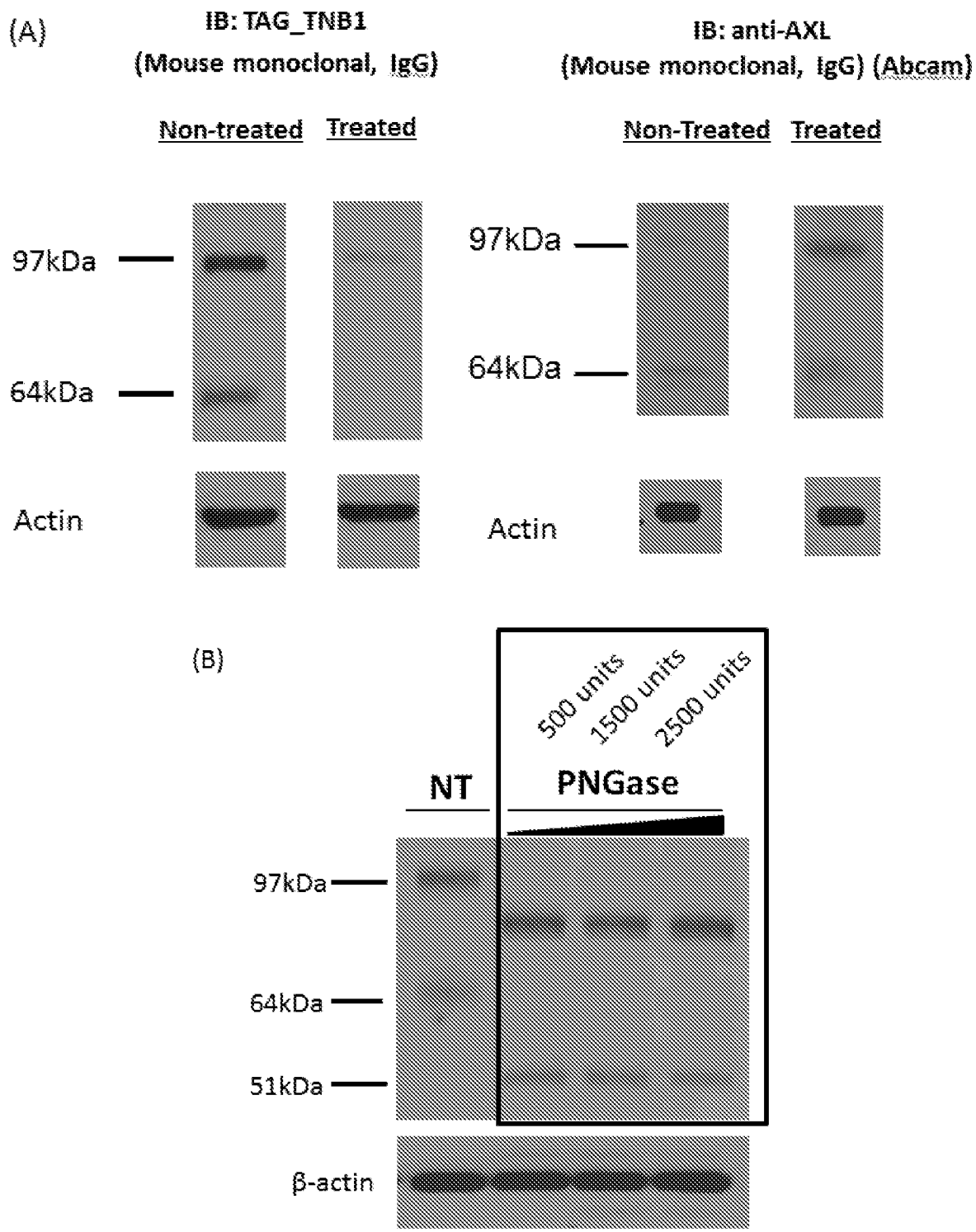
FIG. 4 shows that TAG-TNB1 recognises a glycosylated form of AXL protein. (A) Periodate treatment. TAG_TNB1 binding was significantly reduced post-treatment with sodium metaperiodate (left panel), suggesting binding of TAG_TNB1 was glycan dependent. In contrast, commercial anti-AXL did not show any reduction in binding intensity (right panel). (B) PNGase treatment. Cell lysate sample were treated with increasing concentrations of PNGase. Immunoblotting of TAG_TNB1 showed that binding of TAG_TNB1 is not N-glycan dependent. Binding of the PNGase treated sample remain strong with reduced molecular weight due to the loss of N-link glycans on protein. (C) b-elimination treatment. Binding of TAG_TNB1 was abolished upon treatment with b-elimination, suggesting mAb binding was O-linked glycan dependent. Experimental control was done with an in-house mAb (known O-linked dependent) and human embryonic stem cell (hESC) lysate. Actin was used a loading control for all experiments. (D) Blocking of cell surface binding with free terminal sugars. Flow cytometry analysis of cell surface binding with TAG_TNB1 with free terminal sugars of Lewis Y and Type 4 B antigen. Partial shift in binding (towards negative control) were observed with both terminal sugar blocking ($2^{nd}$ and $4^{th}$ panel). Shaded: negative control, Dashed line: TAG-TNB1 only; Solid: TNB1 pre-incubated with terminal sugars.
Figure 4:
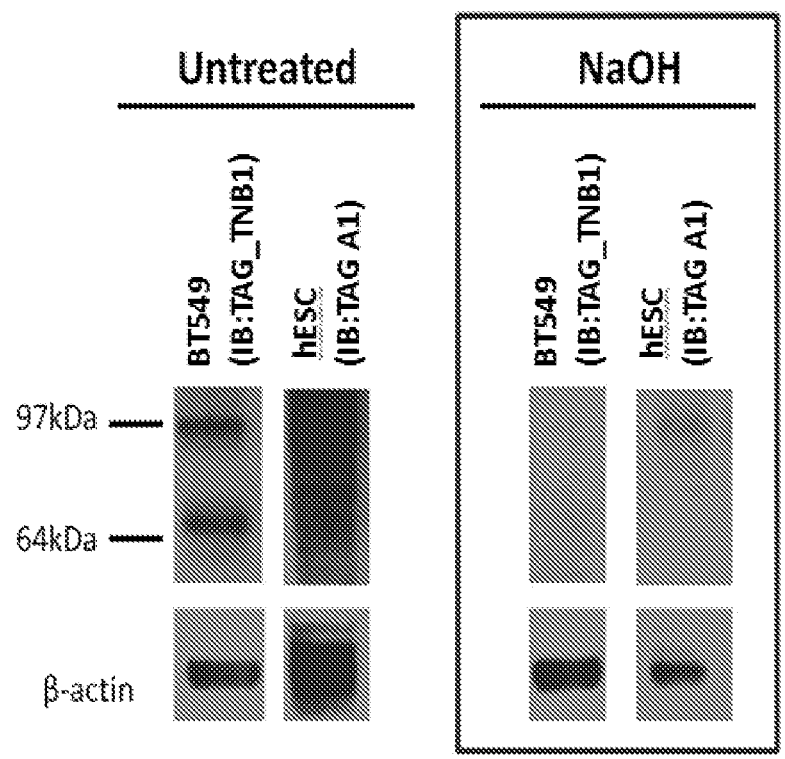
Figure 4:
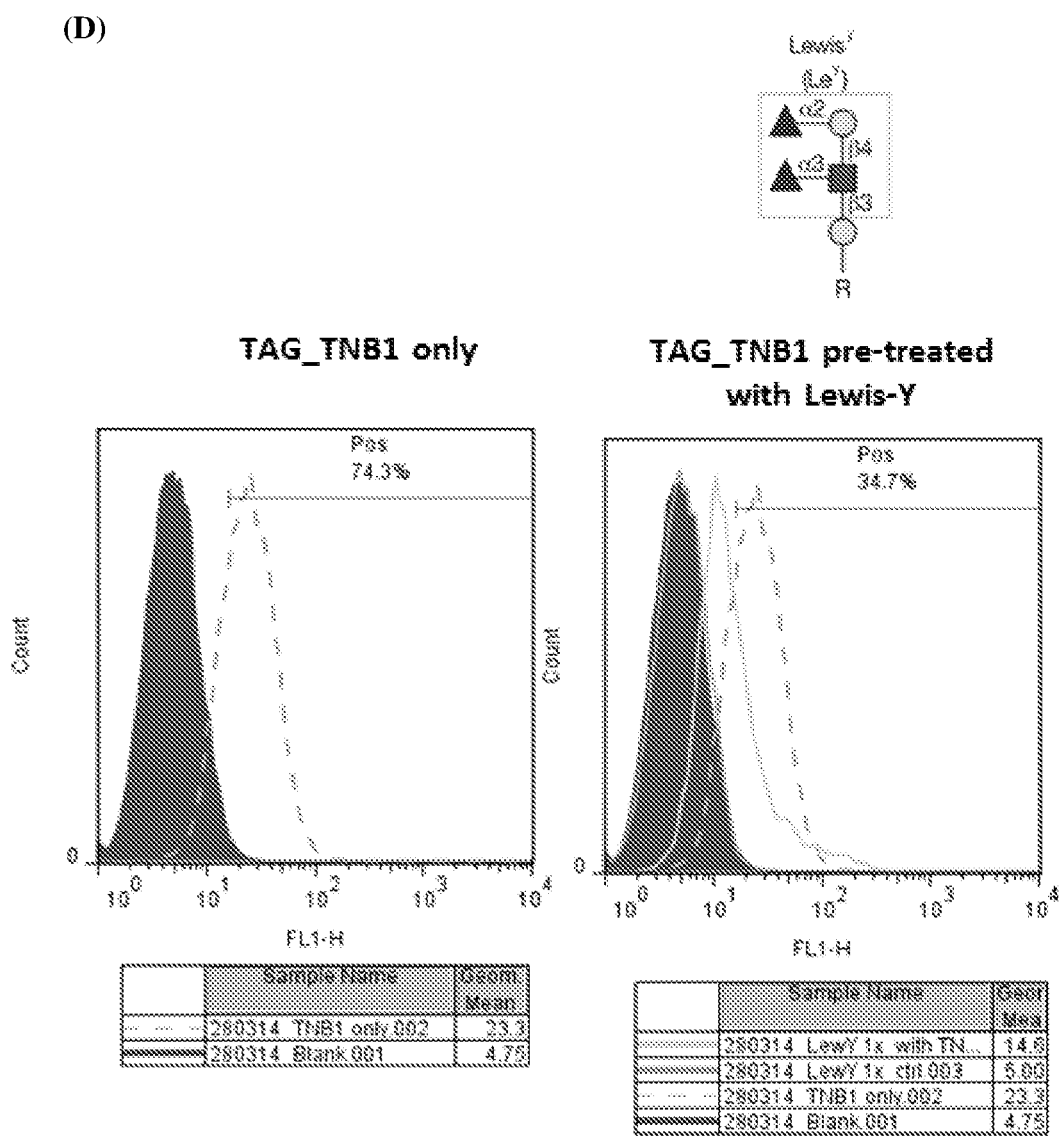
Figure 4:
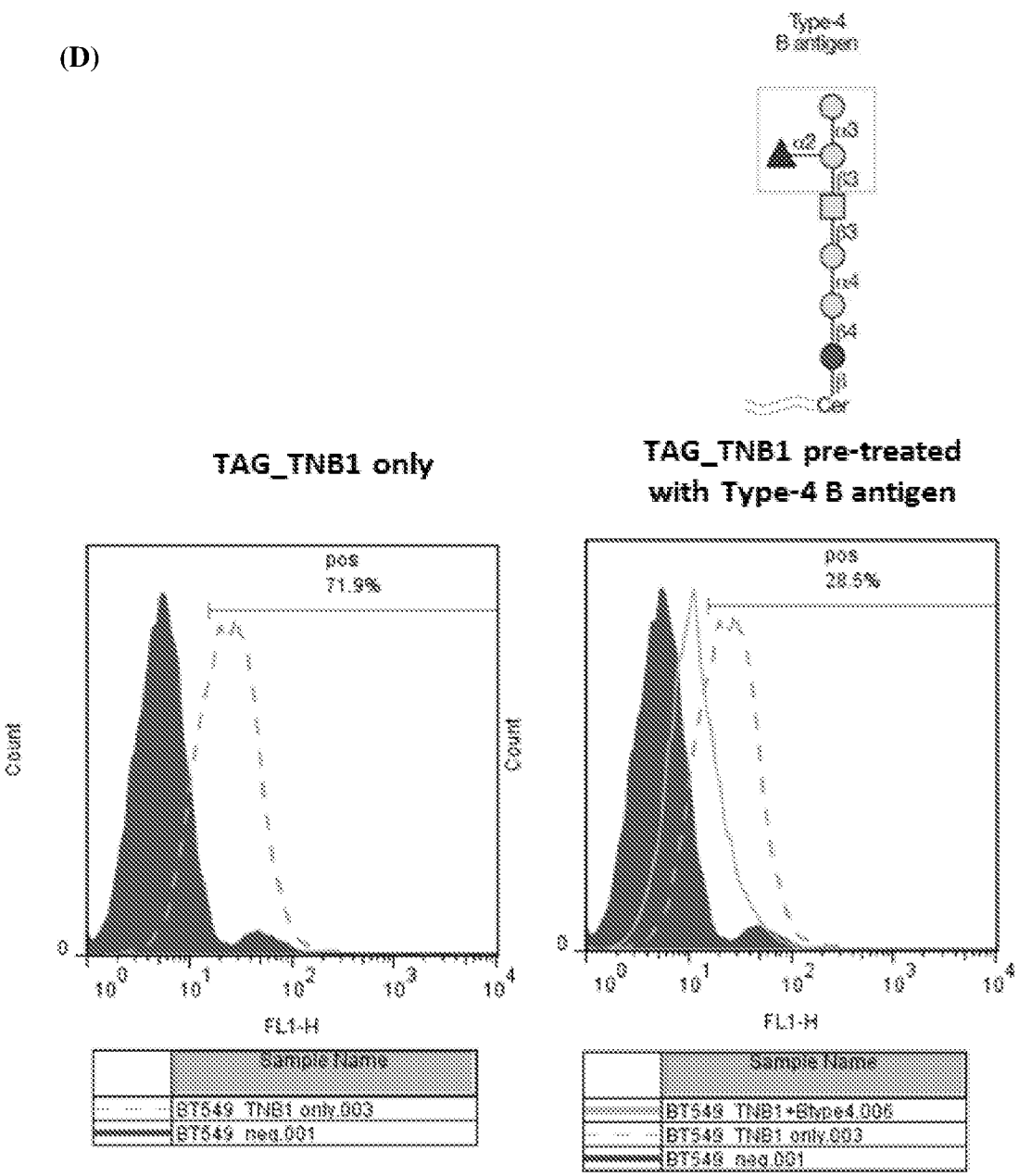

To determine if TAG_TNB1 is targeting a glycan epitope, periodate treatment was carried out. Sodium metaperiodate ($NaIO_4$) breaks the ring structure of saccharide between the vicinal diols to give two aldehyde groups by oxidation. The aldehyde groups are then reduced to hydroxyls by sodium borohydride, $NaBH_4$. This treatment will affect the binding of antibodies that target glycan epitopes. The results from periodate treatment demonstrated that the binding of TAG_TNB1 was significantly reduced when compared to the control without treatment, shown in FIG. 4A (left panel), demonstrating that TAG_TNB1 recognises a glycan epitope on AXL. The treatment of periodate and immunoblotting with commercial anti-AXL antibody did not show any reduction in signal intensity suggesting that the commercial antibody does not recognise a glycan epitope on AXL. To further elucidate if TAG_TNB1 is binding to AXL receptor protein via either N-linked glycan or O-linked glycan group, PNGase treatment and β-elimination assays were used respectively. The enzyme PNGase is able to cleave off all N-linked sugars attached to the antigen. After PNGase treatment, the antigen bands were still observed but at a lower MW (FIG. 4B). This suggests that binding of TAG_TNB1 to its antigen is not N-linked dependent. Actin was used as a loading control. B-elimination using sodium hydroxide (NaOH) was carried out to determine if TAG_TNB1 is binding to its antigen via O-linked glycan. NaOH will hydrolyze all O-linked sugars attached to the antigen. PBS treatment was used as a negative control. In addition, hESC lysate probed with TAG-A1 (in-house) was used as a positive control to ensure the experimental method is correct. After treatment, the antigen bands was absent suggesting that binding of TAG_TNB1 to its antigen is O-linked dependent (FIG. 4C). Actin was again used as a loading control. To determine the terminal glycan epitope TAG_TNB1 may be recognizing, a glycan array analysis was performed data not shown). Terminal glycan with positive signal with TAG_TNB1 were purchased and tested. Blocking of cell surface binding using flow cytometry was observed with terminal sugars Lewis Y and Type 4 B antigen. Partial shift in the histogram binding towards the negative control was seen (FIG. 4D). Taken together, TAG_TNB1 bound to an O-linked glycan specific epitope found on AXL.

Figure 5:
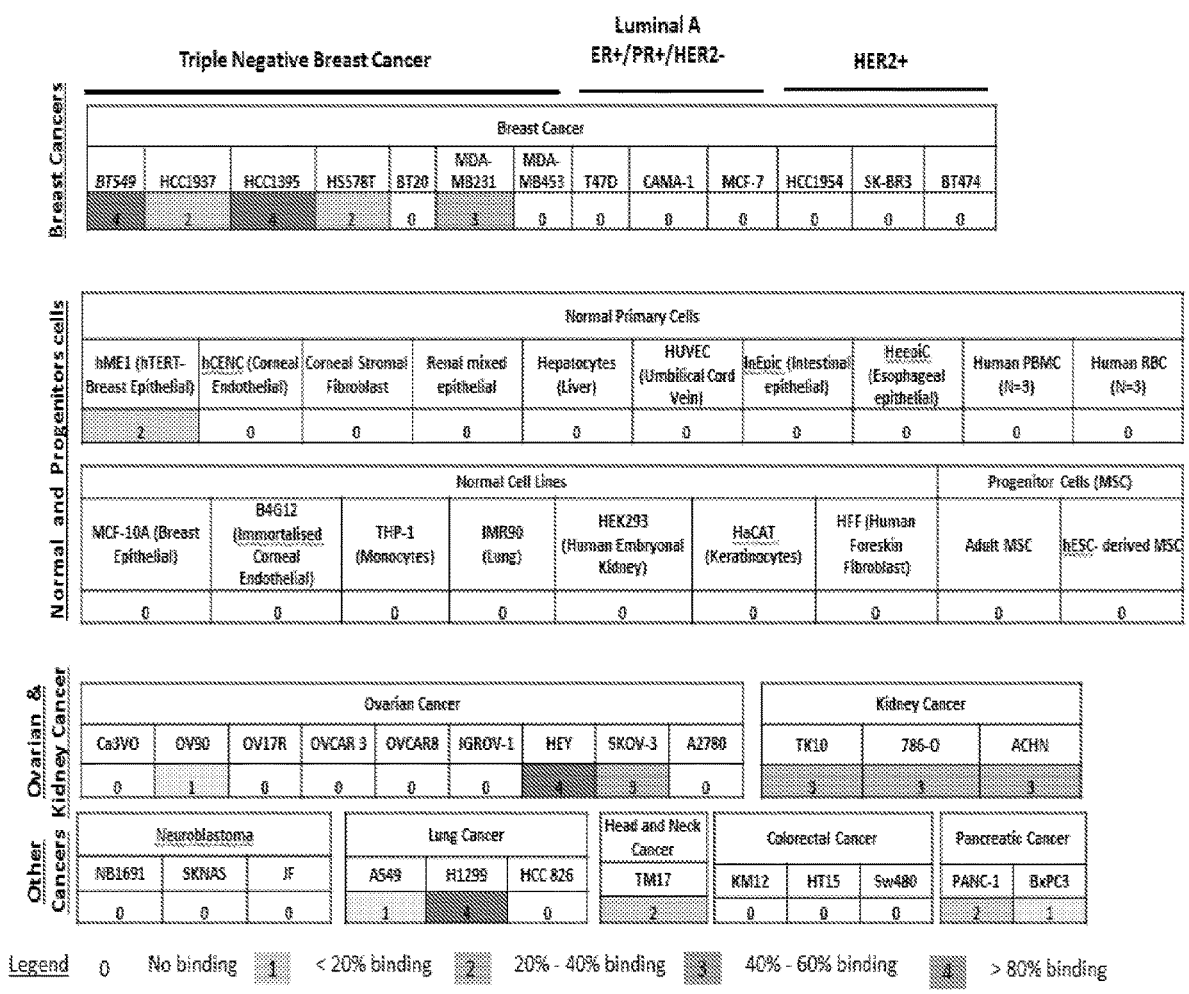
FIG. 5 shows the target prevalence of TAG-TNB1 in cancer and normal cells lines. Flow cytometry analysis of cell surface binding was performed on Breast, Ovarian, Kidney, Lung, Neuroblastoma, Head and Neck, Colorectal, Pancreatic Cancers in addition to normal and progenitor cell lines. Binding shift was determined via m-gating. 0=no binding, 1<20% binding, 2=20%-40% binding, 3=40%-60% binding, 4>80% binding.

The binding specificity of TAG_TNB1 was determined using flow cytometry where live cell surface binding was investigated (FIG. 5). TAG_TNB1 showed strong binding to multiple TNBC cell lines but not Luminal A or HER2 positive breast cancer cells. The lack of binding of TAG_TNB1 to normal (immortalised and primary) and progenitor cells suggests that TAG_TNB1 may be binding to specific subsets of cancer cells. Furthermore, TAG_TNB1 although raised against a TNBC cell line, the binding of the mAb was also observed across multiple cancers including Ovarian, Kidney, Lung, Neuroblastoma, Head and Neck, Colorectal, Pancreatic Cancers. This suggests TAG_TNB1 may be targeting a conserved glycosylated cancer antigen target on AXL receptor tyrosine kinase, that could be found in multiple cancer types and it is more prevalent in TNBC where there are limited treatment options.

Next, the expression of AXL was examined in both TAG_TNB1 binding and non-binding cell lines (FIG. 6). Both mRNA and protein expression of AXL was studied. The cell surface binding profile using flow cytometry of TAG_TNB1 was similar to the results of mRNA and protein expression. The commercial antibodies used also showed similar immunoblot profiles. These result implied that an overexpression of AXL in cancer resulted in the binding of TAG_TNB1. However, the immunoblots with different commercial AXL antibodies displayed different multi-bands profile on the blots. More importantly, TAG_TNB1 binding revealed fewer bands suggesting that TAG_TNB1 is more specific. Actin was used as loading control for the immunoblots.

Figure 7:
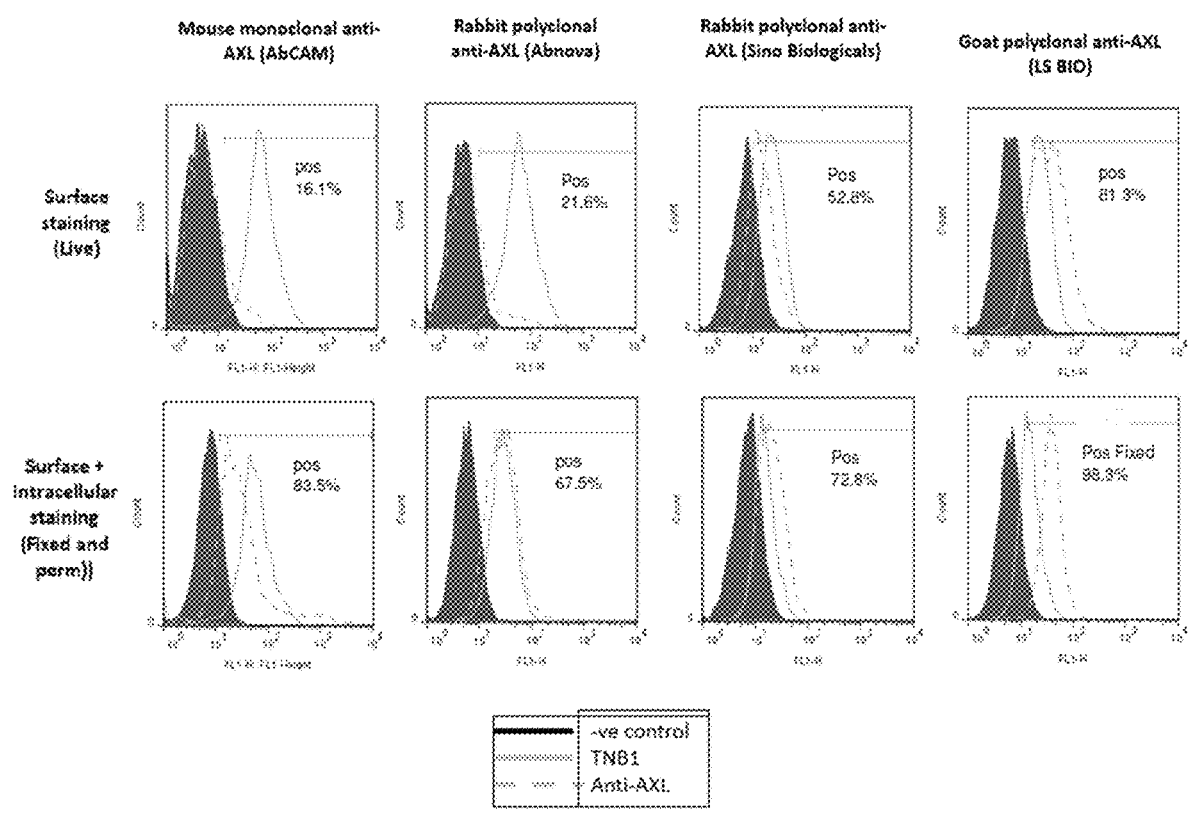
FIG. 7 shows the comparison of TAG_TNB1 with anti-AXL commercial antibodies. Flow cytometry analysis was performed on both cell surface binding and intracellular binding (fixed and perm). Shaded: negative control, Solid: TAG_TNB1 only; Dashed: anti-AXL commercial mAb.
Figure 8:
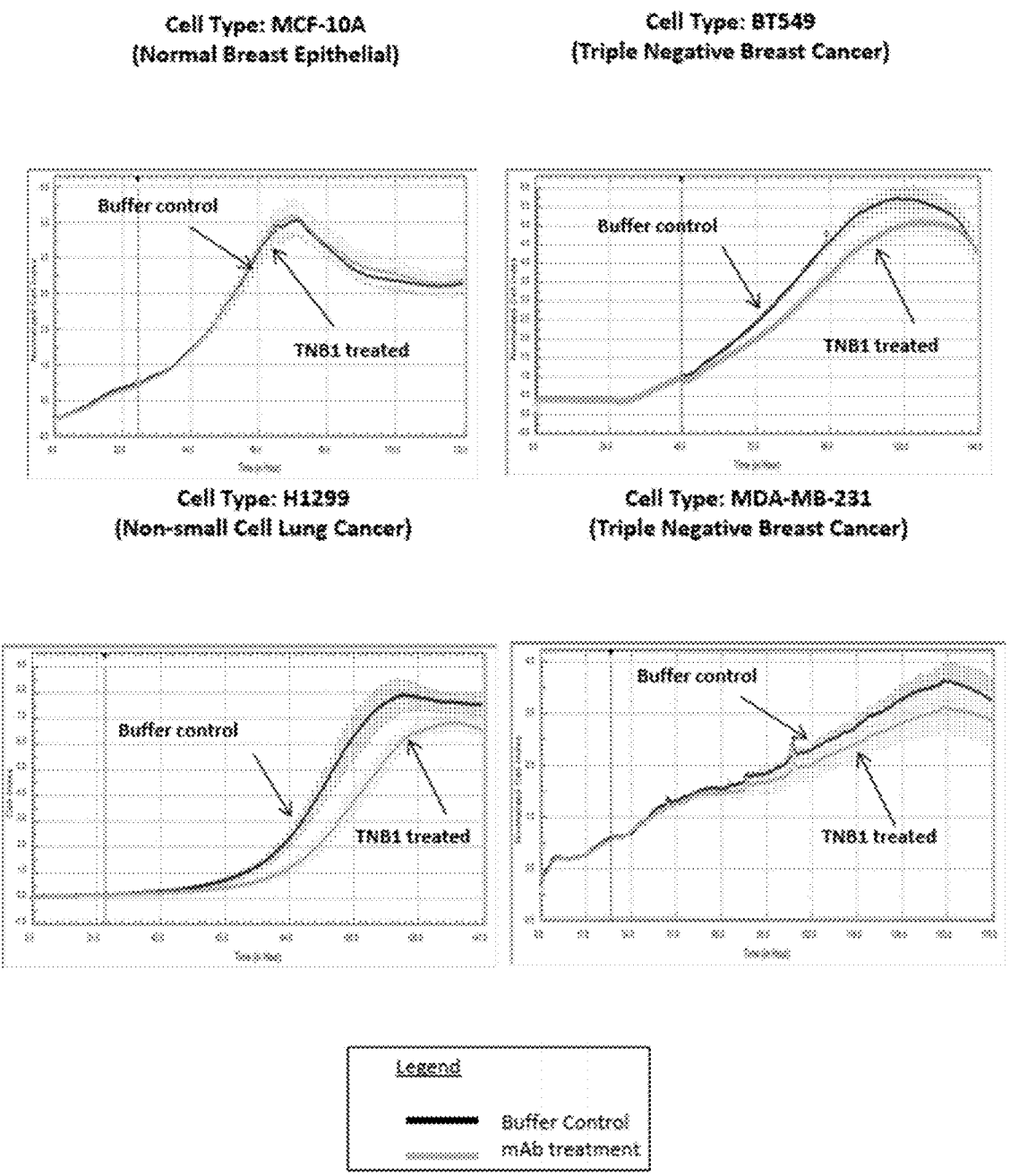
FIG. 8 shows the effect of TAG_TNB1 antibody on proliferation. (A) Inhibition of proliferation of cells using a single dose experiment was performed via the Xcelligence system. Top left: BT549, top right: MDA-MB-231, bottom left: H1299, and bottom right: MCF10A (normal breast epithelial cell). Solid black line: buffer control, Grey line: mAb treatment (100 ng/ul), Straight line down: point when mAb was spiked into the culture.
Figure 9:
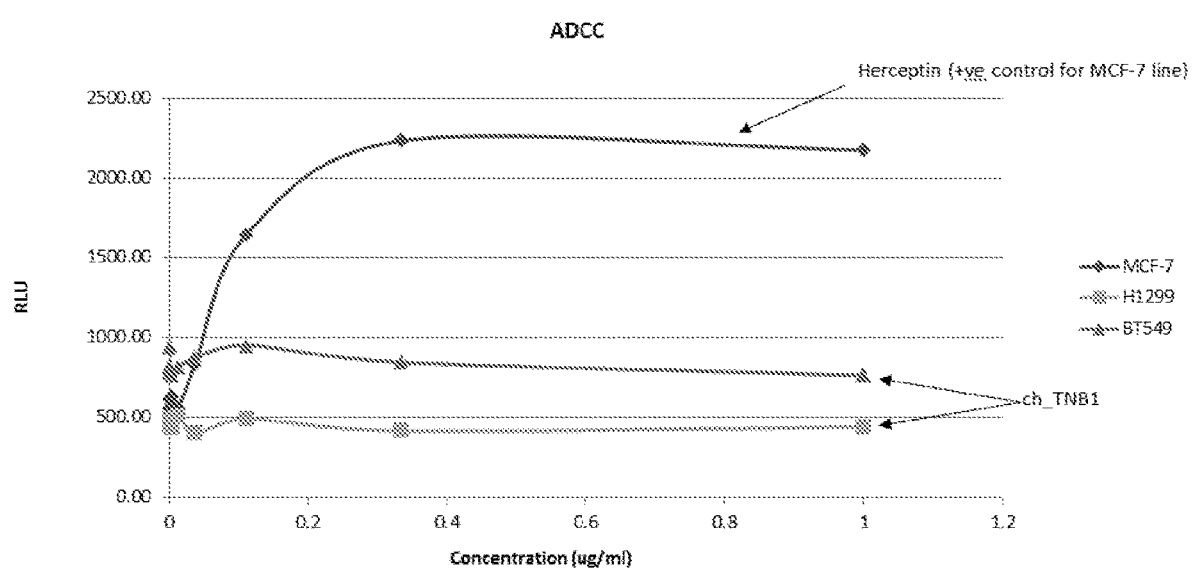
FIG. 9 shows the antibody dependent cellular cytotoxicity (ADCC) effect with chimeric-TAG_TNB1(ch_TNB1). ADCC experiment was performed using the ADCC kit (Promega). Herceptin on MCF-7 cell line was use as positive control. Chimeric_TAG_TNB1 did not show any significant ADCC effect on both TNBC and NSCLC. Circle: MCF-7 with Herceptin; Square: H1299 with ch_TNB1; Triangle: BT549 with ch_TNB1.
Figure 10:
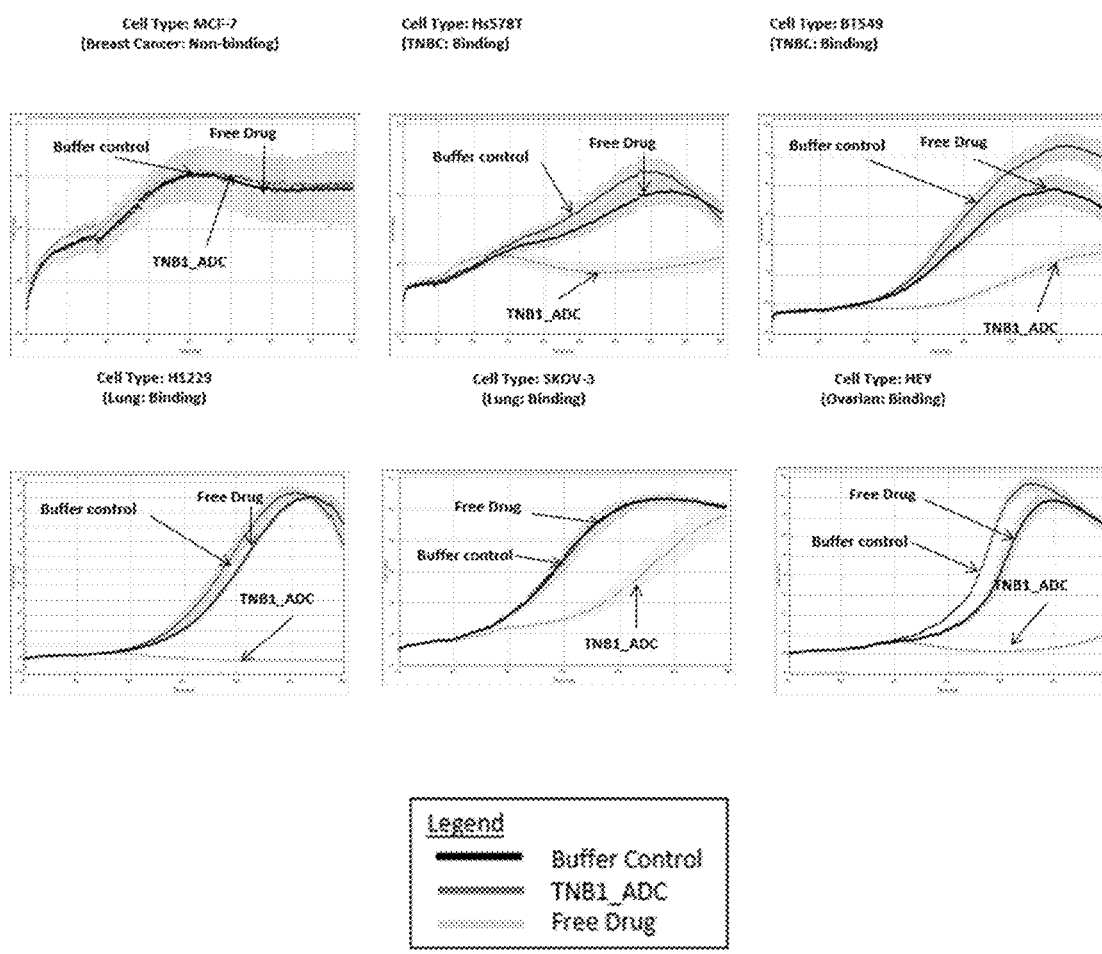
FIG. 10 shows the antibody drug conjugate (ADC) effect of chimeric TAG_TNB1 (ch_TNB1) on cell proliferation. Inhibition of the cell proliferation ch_TNB1 binding and non-binding cell lines via ADC were performed using the Xcellligence system. ch_TNB1 was conjugated with a drug payload (Saporin) and single dose of 10 ng/ul was used to treat the cells ~24 hours post seeding. Number of replicate n=6.
Figure 11:
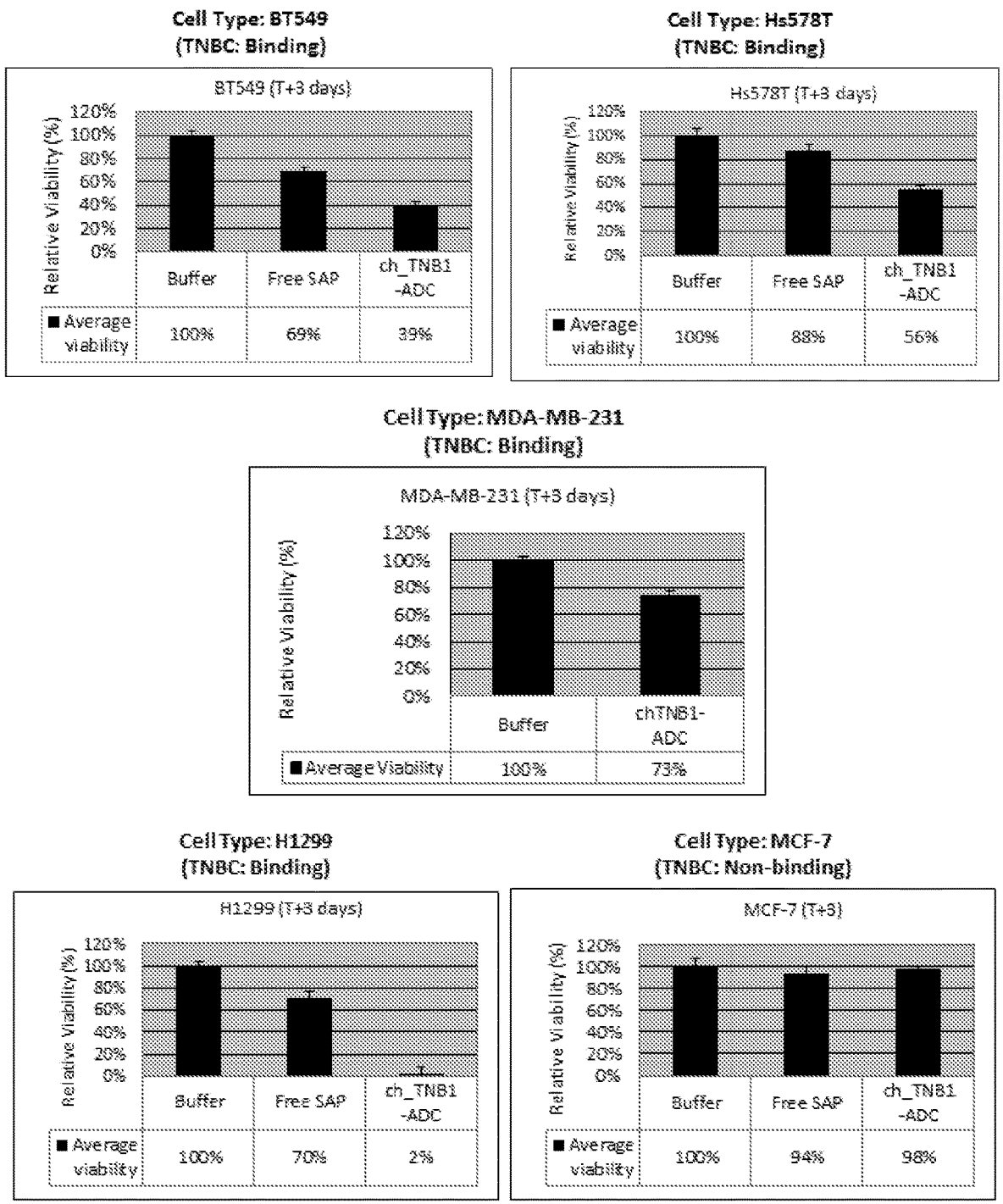
FIG. 11 shows the ADC effect of ch_TNB1 on cell viability. Determination of cell viability of ch_TNB1 conjugated ADC treated cells were measured using Cell Titre Glo assay with both mAb binding and non-binding cells. Single dose of 10 ng/ul was used to treat the cells ~24 hours post seeding and incubated over 3 days post treatment. Number of replicate n=6.
Figure 12:
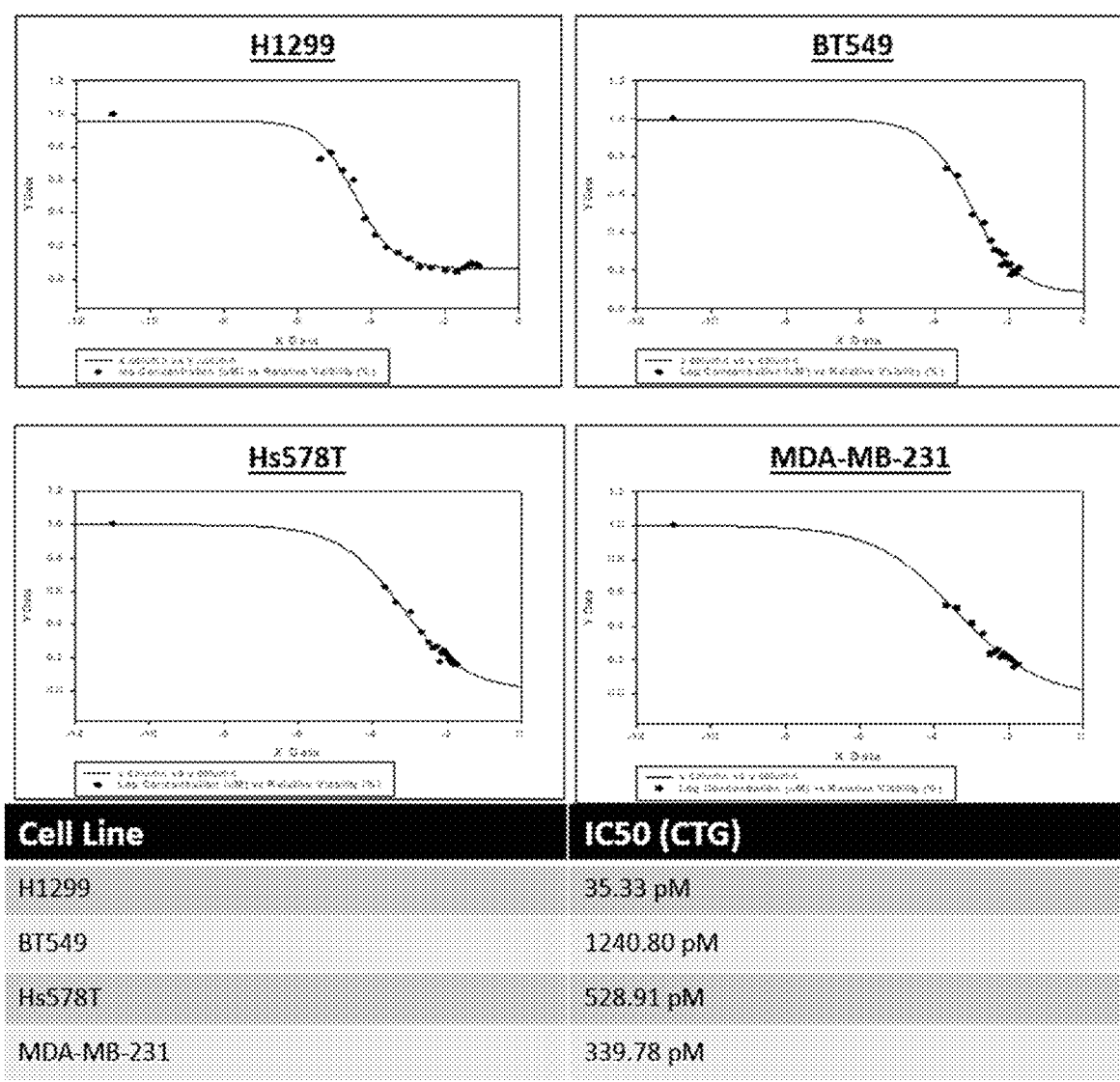
FIG. 12 shows the determination of IC50 for ch_TNB1-ADC conjugate via Cell Titre Glo assay. Single dose of 10 ng/ul was used to treat the cells ~24 hours post seeding and incubated over 3 days post treatment. IC50 of mAb binding cell lines H1299, BT549, Hs578T, MDA-MB-231 was found to be at 35.33 pM, 1240.80 pM, 528.91 pM, and 339.78 pM respectively. Number of replicate n=4.
Figure 13:
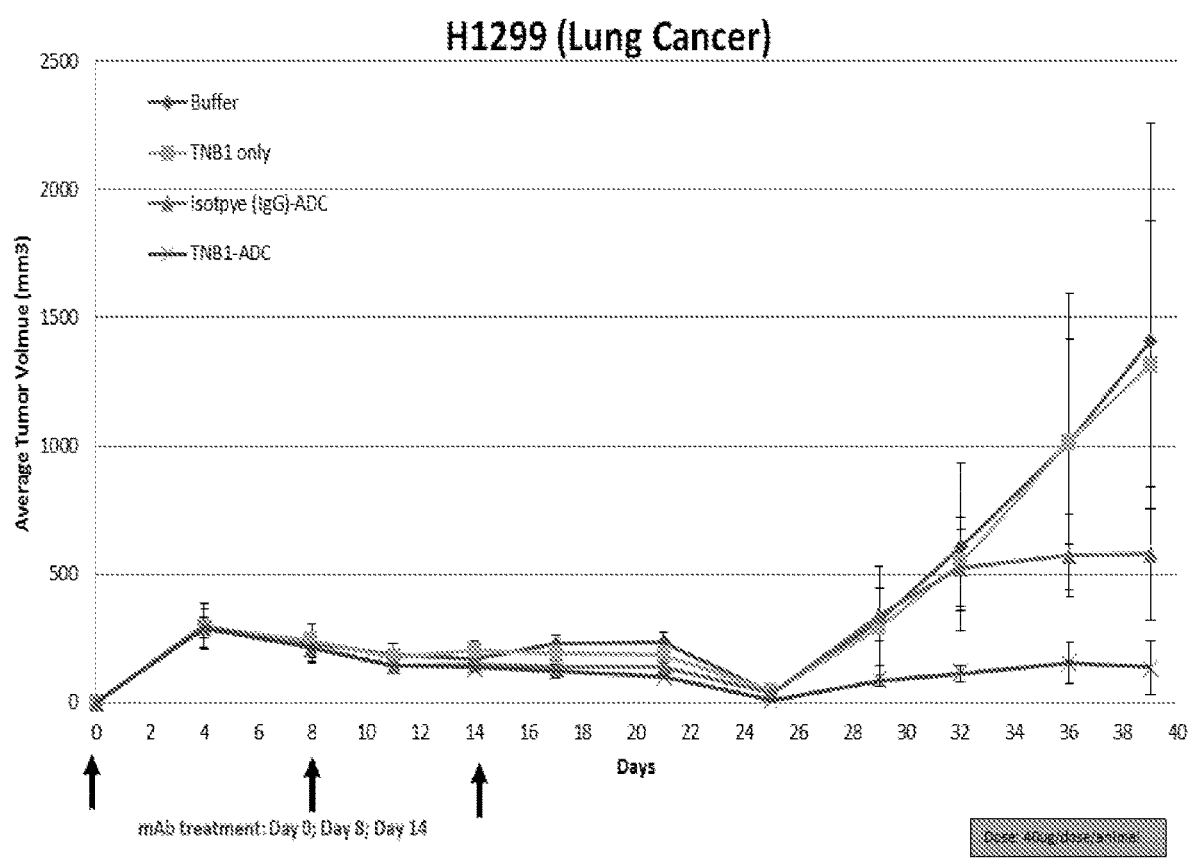
FIG. 13 shows the effect of ch_TNB1-ADC on H1299 in-vivo model. Animals were inoculated with H1299 to form xenograft and mAb treatment was performed. Significant suppression of tumour growth was observed in the ch_TNB1-ADC treated cohort when compared to both the controls buffer only, mAb only (TAG_TNB1 only) control and Isotype (IgG)-ADC control. Each animal cohort has 3 animals. A total of 3 doses of ch_TNB1-ADC (40 ug/dose/animal) were given to the animals at Day 0, Day 8, and Day 14.

Specificity of TAG_TNB1 compared to commercial anti-AXL antibodies was shown in FIG. 7. Flow cytometry analysis was carried out on both the cell surface and intracellular binding specificity of the antibodies. A total of 4 different anti-AXL commercial antibodies were examined. Cell surface binding was observed for only 2 out of the 4 commercial anti-AXL antibodies tested, and both these antibodies were polyclonal antibodies. Intracellular binding of the antibodies via fixation and permeabilization demonstrated that all commercial anti-AXL antibodies bound to the cells.

The therapeutic potential of TAG_TNB1 was investigated by testing its effects on growth inhibition, antibody dependency cellular cytotoxicity (ADCC), and antibody drug conjugate (ADC). The effect of TAG_TNB1 on proliferation of its binding cell lines was observed using the Xcelligence system. In a single dose experiment of 100 ng/ml, TAG_TNB1 demonstrated inhibition of two TNBC cells lines (BT549 and MDA-MB-231) and one NSCLC (H1299). Importantly, at the same dose, the mAb does not affect proliferation of breast normal epithelial cells. Using a surrogate cell system (Promega ADCC kit), the ADCC potential of chimeric TAG_TNB1 (ch_TNB1) was investigated. Clinical grade Herceptin with MCF-7 cell lines was used a positive control to ensure validity of the assay. The ch_TNB1 did not show any significant ADCC effect on both TNBC (BT549) and NSCLC (H1299) cells. The ability of the mAb to be internalised and possibly carry a drug payload was first demonstrated using immunofluorescence with pH-RODO dye. At t=min (4° C.) the mAb was localised at the cell membrane forming a ring around the cells. After 4-8 hrs of incubation at 37° C., antibody binding was observed with punctuated clusters intracellularly (data not shown). Next, ch_TNB1 was directly conjugated with a drug payload (Saporin) and dosing at 10 ng/ml ch_TNB1-ADC demonstrated significant inhibition in cell proliferation with the Xcelligence system on NSCLC, Ovarian and TNBC cells. No ADC effect was observed for MCF-7, a TAG_TNB1 non-binding cell line. To further determine the effect of ADC on cell viability, cells were dose at 10 ng/ml and the cell viability was measured using Cell Titre Glo (CTG) assay. Concurring with the Xcelligence data, significant cell death (>50%) was observed for all the binding cell line and no cell death was observed on the non-binding cells. The IC50 of the mAb conjugate was determine to range from 35.33 pM to 1240.80 pM varying from cell lines.

Finally, mouse tumor xenograft was used to determine the ability of ch_TNB1 to inhibit tumor growth in vivo. In a time course experiment, tumor cells and the first dose of ch_TNB1-ADC were inoculated to the animal on the same day with cells being injected 2 hours prior to mAb. Two additional doses of ch_TNB1-ADC were administered at 7 day intervals (day 7 and 14 respectively) and the growth of the tumours was monitored. Approximately after 25 days, the tumor volume of animals treated with just the buffer, TAG_TNB1 only, and Isotype (IgG)-ADC control (conditions 1, 2 and 3 respectively begin to increase and continued for another 2 weeks. On the other hand, the proliferation of tumors for animals treated with ch_TNB1-ADC was suppressed throughout period of investigation.

What is claimed is:

1. An antigen-binding protein, or an antigen-binding fragment thereof, that binds to AXL receptor tyrosine kinase, comprising (i) a heavy chain variable domain (VH) comprising a VH complementarity determining region (CDR) 1 (VHCDR1) having the amino acid sequence GFTFT-SYYMY (SEQ ID NO: 3), a VHCDR2 having the amino acid sequence GVSPSNGGANFNEKFKT (SEQ ID NO: 4), and a VHCDR3 having the amino acid sequence FLY-GPRYFDV (SEQ ID NO: 5); and (ii) a light chain variable domain (VL) comprising a VL complementarity determining region (CDR) 1 (VLCDR1) having the amino acid sequence RASESVDNYGISFMN (SEQ ID NO: 6), a VLCDR2 having the amino acid sequence QQSKEVPYT (SEQ ID NO: 7), and a VLCDR3 having the amino acid sequence (SEQ ID NO: 8).

2. The antigen-binding protein, or antigen-binding fragment thereof, as claimed in claim 1, wherein the heavy chain variable region comprises the amino acid sequence set forth in SEQ ID NO:1.

3. The antigen-binding protein, or antigen-binding fragment thereof, as claimed in claim 1, wherein the light chain variable region comprises the amino acid sequence set forth in SEQ ID NO:2.

4. The antigen-binding protein, or antigen-binding fragment thereof, as claimed in claim 1, wherein the antigen binding protein is selected from the group consisting of monoclonal, recombinant, polyclonal, chimeric, humanized, bispecific, and heteroconjugate antibodies; and wherein the antigen-binding fragment thereof is selected from the group consisting of a domain antibody, antigen binding fragments, single chain Fv, a single chain antibody, a univalent antibody lacking a hinge region, a minibody, a diabody, and a tandem diabody; optionally wherein the antigen-binding protein is a monoclonal antibody; optionally wherein the monoclonal antibody is humanized.

5. The antigen-binding protein, or antigen-binding fragment thereof, as claimed in claim 1, wherein the antigen-binding protein, or antigen-binding fragment thereof, binds to a glycan on the AXL receptor tyrosine kinase; optionally wherein the glycan is an O-linked glycan.

6. The antigen-binding protein, or an antigen-binding fragment thereof, as claimed in claim 1, comprising a radioisotope or a cytotoxin conjugated thereto; optionally wherein the antigen-binding protein, or antigen-binding fragment, comprising a radioisotope or cytotoxin conjugated thereto is internalized into a cell upon binding to AXL receptor tyrosine kinase.

7. The antigen-binding protein, or antigen-binding fragment thereof, as claimed in claim 6, wherein the antigen-binding protein, or antigen-binding fragment thereof, is conjugated with a cytotoxin selected from the group consisting of monomethyl auristatin E (MMAE-1), mertansine (DM-1) and saporin.

8. The antigen-binding protein, or antigen-binding fragment thereof, as claimed in claim 1, wherein the antigen-binding protein, or antigen-binding fragment thereof, is formulated as a composition comprising a physiologically acceptable carrier.

9. The antigen-binding protein, or antigen-binding fragment thereof as claimed in claim 8, wherein the composition comprises a further active pharmaceutical ingredient selected from the group consisting of bevacizumab, carboplatin, paclitaxel, and gefitinib.

10. The antigen-binding protein, or antigen-binding fragment thereof, as claimed in claim 1, wherein the heavy chain variable region comprises an amino acid sequence that is about 80%, about 85%, about 90%, about 95%, about 96%, about 97%, about 98% or about 99% identical to the heavy chain variable region set forth in SEQ ID NO: 1.

11. The antigen-binding protein, or antigen-binding fragment thereof, as claimed in claim 1, wherein the light chain variable region comprises an amino acid sequence that is about 80%, about 85%, about 90%, about 95%, about 96%, about 97%, about 98% or about 99% identity to the amino acid sequence set forth in SEQ ID NO:2.

12. The antigen-binding protein, or antigen-binding fragment thereof, as claimed in claim 4, wherein the antigen binding protein, or antigen binding fragment thereof, is a humanized monoclonal antibody.

13. An antibody that comprises a heavy chain variable region comprising the amino acid sequence set forth in SEQ ID NO: 1 and a light chain variable region comprising the amino acid sequence set forth in SEQ ID NO: 2.

14. A method of treating an AXL-expressing cancer comprising administering an antigen-binding protein, or an antigen-binding fragment thereof, that binds to AXL receptor tyrosine kinase, to a subject in need thereof, wherein the antigen-binding protein, or the antigen-binding fragment thereof, comprises (i) a heavy chain variable domain (VH) comprising a VH complementarity determining region (CDR) 1 (VHCDR1) having the amino acid sequence GFTFTSYYMY (SEQ ID NO: 3); a VHCDR2 having the amino acid sequence GVSPSNGGANFNEKFKT (SEQ ID NO: 4), and a VHCDR3 having the amino acid sequence FLYGPRYFDV (SEQ ID NO: 5); and (ii) a light chain variable domain (VL) comprising a VL complementarity determining region (CDR) 1 (VLCDR1) having the amino acid sequence RASESVDNYGISFMN (SEQ ID NO: 6), a VLCDR2 having the amino acid sequence GASNQGS (SEQ ID NO: 7), and a VLCDR3 having the amino acid sequence QQSKEVPYT (SEQ ID NO: 8), to thereby treat the AXL-expressing cancer.

15. The method of claim 14, wherein the cancer is selected from the group consisting of triple-negative breast cancer, non-small cell lung cancer, ovarian cancer, kidney cancer, and pancreatic cancer.

16. The method of claim 14, wherein the antigen-binding protein, or the antigen-binding fragment thereof, is conjugated with a radioisotope or a cytotoxin.

17. The method of claim 14, wherein the method comprises administering a further active pharmaceutical ingredient to the subject; optionally wherein the further pharmaceutical agent is administered separately, simultaneously or sequentially.

18. The method of claim 14, wherein the antigen-binding protein, or an antigen-binding fragment thereof, is administered with chemotherapy; optionally wherein the chemotherapy is administered separately, simultaneously or sequentially.

* * * * *

SEQUENCE LISTING

```
<160> NUMBER OF SEQ ID NOS: 15

<210> SEQ ID NO 1
<211> LENGTH: 119
<212> TYPE: PRT
<213> ORGANISM: Artificial Sequence
<220> FEATURE:
<223> OTHER INFORMATION: Isolated peptide sequence

<400> SEQUENCE: 1

Gln Val Lys Leu Gln Glu Ser Gly Ala Glu Leu Val Lys Pro Gly Ala
1               5                   10                  15

Ser Val Lys Leu Ser Cys Lys Ala Ser Gly Phe Thr Phe Thr Ser Tyr
            20                  25                  30

Tyr Met Tyr Trp Val Lys Gln Arg Pro Gly Gln Gly Leu Glu Trp Ile
        35                  40                  45

Gly Gly Val Ser Pro Ser Asn Gly Ala Asn Phe Asn Glu Lys Phe
    50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Phe Leu Tyr Gly Pro Arg Tyr Phe Asp Val Trp Gly Gln Gly
                100                 105                 110
```

Thr Thr Val Thr Val Ser Ser
        115

<210> SEQ ID NO 2
<211> LENGTH: 111
<212> TYPE: PRT
<213> ORGANISM: Artificial Sequence
<220> FEATURE:
<223> OTHER INFORMATION: Isolated peptide sequence

<400> SEQUENCE: 2

Asp Ile Glu Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Gly Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys
            100                 105                 110

<210> SEQ ID NO 3
<211> LENGTH: 10
<212> TYPE: PRT
<213> ORGANISM: Artificial Sequence
<220> FEATURE:
<223> OTHER INFORMATION: Isolated peptide sequence

<400> SEQUENCE: 3

Gly Phe Thr Phe Thr Ser Tyr Tyr Met Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Isolated peptide sequence

<400> SEQUENCE: 4

Gly Val Ser Pro Ser Asn Gly Gly Ala Asn Phe Asn Glu Lys Phe Lys
1               5                   10                  15

Thr

<210> SEQ ID NO 5
<211> LENGTH: 10
<212> TYPE: PRT
<213> ORGANISM: Artificial Sequence
<220> FEATURE:
<223> OTHER INFORMATION: Isolated peptide sequence

<400> SEQUENCE: 5

Phe Leu Tyr Gly Pro Arg Tyr Phe Asp Val
1               5                   10

<210> SEQ ID NO 6
<211> LENGTH: 15

```
<212> TYPE: PRT
<213> ORGANISM: Artificial Sequence
<220> FEATURE:
<223> OTHER INFORMATION: Isolated peptide sequence

<400> SEQUENCE: 6

Arg Ala Ser Glu Ser Val Asp Asn Tyr Gly Ile Ser Phe Met Asn
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Isolated peptide sequence

<400> SEQUENCE: 7

Gly Ala Ser Asn Gln Gly Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Isolated peptide sequence

<400> SEQUENCE: 8

Gln Gln Ser Lys Glu Val Pro Tyr Thr
1               5

<210> SEQ ID NO 9
<211> LENGTH: 20
<212> TYPE: DNA
<213> ORGANISM: Artificial Sequence
<220> FEATURE:
<223> OTHER INFORMATION: Primer sequence

<400> SEQUENCE: 9
ggtggctgtg aagacgatga                                            20

<210> SEQ ID NO 10
<211> LENGTH: 20
<212> TYPE: DNA
<213> ORGANISM: Artificial Sequence
<220> FEATURE:
<223> OTHER INFORMATION: Primer sequence

<400> SEQUENCE: 10
ctcagatact ccatgccact                                            20

<210> SEQ ID NO 11
<211> LENGTH: 21
<212> TYPE: DNA
<213> ORGANISM: Artificial Sequence
<220> FEATURE:
<223> OTHER INFORMATION: siRNA sequence

<400> SEQUENCE: 11
cagcgagauu uaugacuaut t                                          21

<210> SEQ ID NO 12
<211> LENGTH: 357
<212> TYPE: DNA
<213> ORGANISM: Artificial Sequence
<220> FEATURE:
<223> OTHER INFORMATION: Isolated genetic sequence
```

<400> SEQUENCE: 12

```
caggtcaaac tgcaggagtc aggggctgaa ctggtgaagc ctggggcttc agtgaagttg      60
tcctgtaagg cttctggctt caccttcacc agctactata tgtactgggt gaagcagagg     120
cctggacaag gccttgagtg gattgggggg gttagtccta gcaatggtgg tgctaacttc     180
aatgagaagt tcaagaccaa ggccacactg actgtagaca atcctccag cacagcctac      240
atgcaactca gcagcctgac atctgaggac tctgcggtct attactgtac aagattcctt     300
tatggtccga ggtacttcga tgtctggggc caagggacca cggtcaccgt ctcctca        357
```

<210> SEQ ID NO 13
<211> LENGTH: 334
<212> TYPE: DNA
<213> ORGANISM: Artificial Sequence
<220> FEATURE:
<223> OTHER INFORMATION: Isolated genetic sequence

<400> SEQUENCE: 13

```
gacattgagc tcacccagtc tccagcttct ttggctgtgt ctctagggca gagggccacc      60
atctcctgca gagccagcga aagtgttgat aattatggca ttagtttat gaactggttc     120
caacagaaac caggacagcc acccaaactc ctcatttatg gtgcatccaa ccagggatcc     180
ggggtccctg ccaggtttag tggcagtggg tctgggacag acttcagcct caacatccat     240
cctatggagg aggatgatac tgcaatgtat ttctgtcagc aaagtaagga ggttccgtac     300
acgttcggag gggggaccaa gctggaaata aaac                                 334
```

<210> SEQ ID NO 14
<211> LENGTH: 894
<212> TYPE: PRT
<213> ORGANISM: Homo sapiens

<400> SEQUENCE: 14

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
```

```
               180                 185                 190
His Val Pro Gly Leu Asn Lys Thr Ser Ser Phe Ser Cys Glu Ala His
            195                 200                 205
Asn Ala Lys Gly Val Thr Thr Ser Arg Thr Ala Thr Ile Thr Val Leu
        210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asn Asp Gly Met Gly Ile Gln
            260                 265                 270
Ala Gly Glu Pro Asp Pro Pro Glu Glu Pro Leu Thr Ser Gln Ala Ser
        275                 280                 285
Val Pro Pro His Gln Leu Arg Leu Gly Ser Leu His Pro His Thr Pro
    290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
        355                 360                 365
Leu Ala Tyr Gln Gly Gln Asp Thr Pro Glu Val Leu Met Asp Ile Gly
    370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
            420                 425                 430
Pro Val His Gln Leu Val Lys Glu Pro Ser Thr Pro Ala Phe Ser Trp
        435                 440                 445
Pro Trp Trp Tyr Val Leu Leu Gly Ala Val Val Ala Ala Ala Cys Val
    450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                485                 490                 495
Arg Tyr Arg Val Arg Lys Ser Tyr Ser Arg Arg Thr Thr Glu Ala Thr
            500                 505                 510
Leu Asn Ser Leu Gly Ile Ser Glu Glu Leu Lys Glu Lys Leu Arg Asp
        515                 520                 525
Val Met Val Asp Arg His Lys Val Ala Leu Gly Lys Thr Leu Gly Glu
    530                 535                 540
Gly Glu Phe Gly Ala Val Met Glu Gly Gln Leu Asn Gln Asp Asp Ser
545                 550                 555                 560
Ile Leu Lys Val Ala Val Lys Thr Met Lys Ile Ala Ile Cys Thr Arg
                565                 570                 575
Ser Glu Leu Glu Asp Phe Leu Ser Glu Ala Val Cys Met Lys Glu Phe
            580                 585                 590
Asp His Pro Asn Val Met Arg Leu Ile Gly Val Cys Phe Gln Gly Ser
        595                 600                 605
```

```
Glu Arg Glu Ser Phe Pro Ala Pro Val Val Ile Leu Pro Phe Met Lys
            610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 15
<211> LENGTH: 894
<212> TYPE: PRT
<213> ORGANISM: Homo sapiens

<400> SEQUENCE: 15

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
```

```
            85                  90                  95
Ile Val Val Ser Gln Leu Arg Ile Thr Ser Leu Gln Leu Ser Asp Thr
                100                 105                 110
Gly Gln Tyr Gln Cys Leu Val Phe Leu Gly His Gln Thr Phe Val Ser
                115                 120                 125
Gln Pro Gly Tyr Val Gly Leu Glu Gly Leu Pro Tyr Phe Leu Glu Glu
            130                 135                 140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
                180                 185                 190
His Val Pro Gly Leu Asn Lys Thr Ser Ser Phe Ser Cys Glu Ala His
                195                 200                 205
Asn Ala Lys Gly Val Thr Thr Ser Arg Thr Ala Thr Ile Thr Val Leu
            210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asn Asp Gly Met Gly Ile Gln
                260                 265                 270
Ala Gly Glu Pro Asp Pro Pro Glu Glu Pro Leu Thr Ser Gln Ala Ser
                275                 280                 285
Val Pro Pro His Gln Leu Arg Leu Gly Ser Leu His Pro His Thr Pro
            290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
                340                 345                 350
Trp Gln Glu Pro Arg Ala Pro Leu Gln Gly Thr Leu Leu Gly Tyr Arg
            355                 360                 365
Leu Ala Tyr Gln Gly Gln Asp Thr Pro Glu Val Leu Met Asp Ile Gly
            370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
                420                 425                 430
Pro Val His Gln Leu Val Lys Glu Pro Ser Thr Pro Ala Phe Ser Trp
            435                 440                 445
Pro Trp Trp Tyr Val Leu Leu Gly Ala Val Val Ala Ala Ala Cys Val
            450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                485                 490                 495
Arg Tyr Arg Val Arg Lys Ser Tyr Ser Arg Arg Thr Thr Glu Ala Thr
                500                 505                 510
```

```
Leu Asn Ser Leu Gly Ile Ser Glu Glu Leu Lys Glu Lys Leu Arg Asp
        515                 520                 525
Val Met Val Asp Arg His Lys Val Ala Leu Gly Lys Thr Leu Gly Glu
        530                 535                 540
Gly Glu Phe Gly Ala Val Met Glu Gly Gln Leu Asn Gln Asp Asp Ser
545                 550                 555                 560
Ile Leu Lys Val Ala Val Lys Thr Met Lys Ile Ala Ile Cys Thr Arg
                565                 570                 575
Ser Glu Leu Glu Asp Phe Leu Ser Glu Ala Val Cys Met Lys Glu Phe
                580                 585                 590
Asp His Pro Asn Val Met Arg Leu Ile Gly Val Cys Phe Gln Gly Ser
        595                 600                 605
Glu Arg Glu Ser Phe Pro Ala Pro Val Val Ile Leu Pro Phe Met Lys
        610                 615                 620
His Gly Asp Leu His Ser Phe Leu Leu Tyr Ser Arg Leu Gly Asp Gln
625                 630                 635                 640
Pro Val Tyr Leu Pro Thr Gln Met Leu Val Lys Phe Met Ala Asp Ile
                645                 650                 655
Ala Ser Gly Met Glu Tyr Leu Ser Thr Lys Arg Phe Ile His Arg Asp
                660                 665                 670
Leu Ala Ala Arg Asn Cys Met Leu Asn Glu Asn Met Ser Val Cys Val
        675                 680                 685
Ala Asp Phe Gly Leu Ser Lys Lys Ile Tyr Asn Gly Asp Tyr Tyr Arg
        690                 695                 700
Gln Gly Arg Ile Ala Lys Met Pro Val Lys Trp Ile Ala Ile Glu Ser
705                 710                 715                 720
Leu Ala Asp Arg Val Tyr Thr Ser Lys Ser Asp Val Trp Ser Phe Gly
                725                 730                 735
Val Thr Met Trp Glu Ile Ala Thr Arg Gly Gln Thr Pro Tyr Pro Gly
                740                 745                 750
Val Glu Asn Ser Glu Ile Tyr Asp Tyr Leu Arg Gln Gly Asn Arg Leu
        755                 760                 765
Lys Gln Pro Ala Asp Cys Leu Asp Gly Leu Tyr Ala Leu Met Ser Arg
        770                 775                 780
Cys Trp Glu Leu Asn Pro Gln Asp Arg Pro Ser Phe Thr Glu Leu Arg
785                 790                 795                 800
Glu Asp Leu Glu Asn Thr Leu Lys Ala Leu Pro Pro Ala Gln Glu Pro
                805                 810                 815
Asp Glu Ile Leu Tyr Val Asn Met Asp Glu Gly Gly Gly Tyr Pro Glu
                820                 825                 830
Pro Pro Gly Ala Ala Gly Gly Ala Asp Pro Pro Thr Gln Pro Asp Pro
        835                 840                 845
Lys Asp Ser Cys Ser Cys Leu Thr Ala Ala Glu Val His Pro Ala Gly
        850                 855                 860
Arg Tyr Val Leu Cys Pro Ser Thr Thr Pro Ser Pro Ala Gln Pro Ala
865                 870                 875                 880
Asp Arg Gly Ser Pro Ala Ala Pro Gly Gln Glu Asp Gly Ala
                885                 890
```